(12) United States Patent
Ohkawa et al.

(10) Patent No.: US 6,583,146 B1
(45) Date of Patent: Jun. 24, 2003

(54) THIAZOLOPYRIMIDINE COMPOUNDS, ITS PRODUCTION AND USE

(75) Inventors: Shigenori Ohkawa, Takatsuki (JP); Naoyuki Kanzaki, Ibaraki (JP); Seiji Miwatashi, Ikeda (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/889,139

(22) PCT Filed: Jan. 27, 2000

(86) PCT No.: PCT/JP00/00395

§ 371 (c)(1),
(2), (4) Date: Jul. 12, 2001

(87) PCT Pub. No.: WO00/44756

PCT Pub. Date: Aug. 3, 2000

(30) Foreign Application Priority Data

Jan. 28, 1999 (JP) ............................................. 11-019828

(51) Int. Cl.⁷ ..................... A61K 31/519; C07D 513/04
(52) U.S. Cl. ................. 514/258; 514/228.5; 514/225.8; 514/233.2; 514/232.5; 514/252.02; 514/252.16; 514/255.05; 514/259; 514/261; 544/278; 544/264; 544/235; 544/237; 544/238; 544/117; 544/102; 544/80; 544/61; 544/58.6; 544/35
(58) Field of Search .................. 544/278, 264, 544/238, 80, 35; 514/258, 259, 261, 252.02, 252.16, 233.2

(56) References Cited

U.S. PATENT DOCUMENTS

| 3,919,201 A | 11/1975 | Evans ........................ 260/305 |
| 4,237,136 A | 12/1980 | Herrling |

FOREIGN PATENT DOCUMENTS

WO 97/33879 9/1997

OTHER PUBLICATIONS

Jiang et al., "Structure–Activity Relationships of 4-(Phenylethynyl)-6-phenyl-1,4-dihydropyridines as Highly Selective A₃ Adenosine Receptor Antagonists"., Med. Chem. 1997, vol. 40, pp. 2596–2608.
Biochem. Pharmacol., vol. 37, No. 4, 1988, pp. 655–664.

Primary Examiner—John M. Ford
(74) Attorney, Agent, or Firm—Wenderoth, Lind & Ponack, L.L.P.

(57) ABSTRACT

Compounds represented by general formula (I):

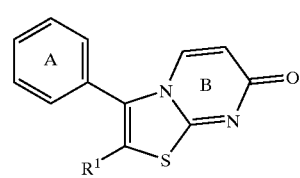

and salts thereof, exhibiting excellent adenosine $A_3$ receptor antagonism: wherein A is an optionally substituted benzene ring; B may be further substituted; and $R^1$ is an optionally substituted cyclic group.

23 Claims, No Drawings

THIAZOLOPYRIMIDINE COMPOUNDS, ITS PRODUCTION AND USE

TECHNICAL FIELD

The present invention relates to novel thiazolopyrimidine compounds having excellent adenosine $A_3$ receptor antagonistic activity, their production, pharmaceutical compositions comprising them, and the like.

BACKGROUND ART

As subtypes of adenosine receptors, $A_1$, $A_{2a}$, $A_{2b}$ and $A_3$ are known. Adenosine induces bronchial constriction in asthma patients, while theophylline, which is known as an antiasthmatic, antagonizes adenosine. Recently several reports showed that activation of adenosine $A_3$ receptors in rats promotes degranulation of mast cells [Journal of Biological Chemistry, 268, 16887–16890 (1993)], that adenosine $A_3$ receptors exist on peripheral blood eosinophils and that the stimulation of adenosine $A_3$ receptors activates phospholipase C and elevates intracellular calcium concentration [Blood, 88, 3569–3574 (1996)].

Currently, as selective adenosine $A_3$ receptor antagonists, xanthine derivatives are reported in GB-A-2288733 and WO 95/11681, and the following compounds are reported in Journal of Medicinal Chemistry, 40, 2596–2608(1997).

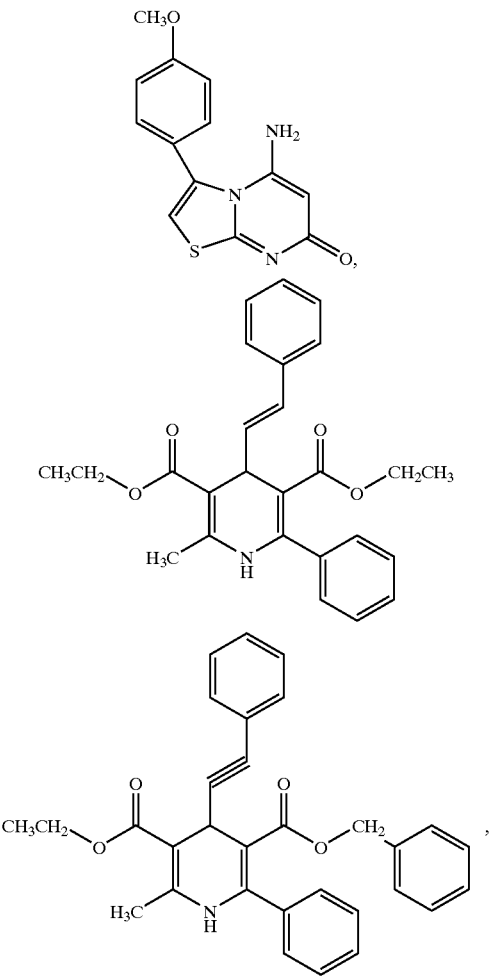

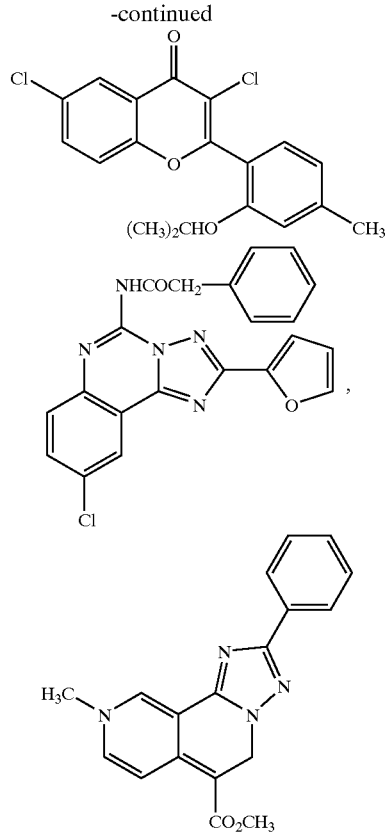

WO 97/33879 discloses an adenosine $A_3$ receptor antagonist comprising a compound of the formula:

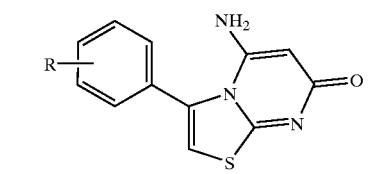

wherein R is hydrogen, chlorine, bromine, fluorine, iodine, hydroxy, $C_{1-4}$ alkyl, $C_{1-4}$ alkoxy or $C_{1-4}$ alkylcarboxy, or a salt thereof and, specifically discloses

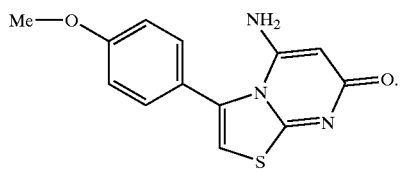

On the other hand, as for thiazolopyrimidine compounds, the following compounds are reported.

1) As a compound having immunostimulating activity, a compound represented by the formula:

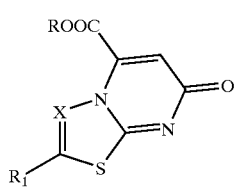

wherein X is nitrogen atom or $R_2$—C group, R is hydrogen atom, a pharmaceutically acceptable cation or alkyl group ($C_{1-5}$), $R_1$ and $R_2$ are the same and different and are hydrogen atom, alkyl group ($C_{1-5}$) or, aralkyl, phenyl, thienyl or pyridyl group optionally substituted with halogen atom, alkyl or alkoxy (the number of carbon atom of alkyl being up to 4) or cycloalkyl group ($C_{1-5}$), or a pharmaceutically acceptable salt, and specifically, the following compounds.

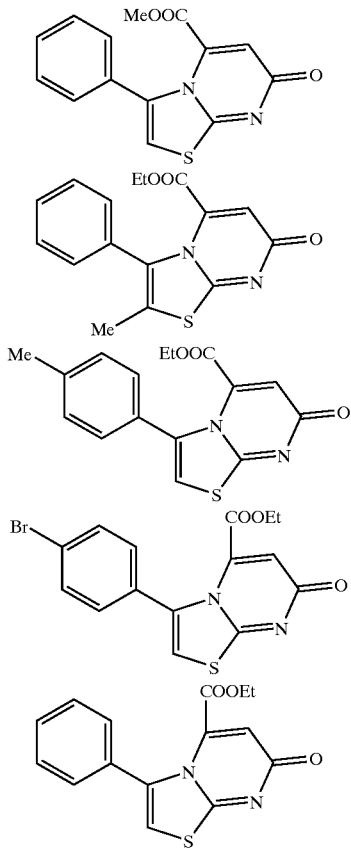

(JP 52-148096 A)

2) As a compound having anti-inflammatory activity, a compound represented by the formula:

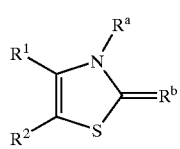

wherein (a) $R^a$ together with $R^b$ forms —C($R^3$)=CH—CO—N= or (b) $R^a$ is hydrogen atom and $R^b$ is =N—CO—CH=CH—$NR^7R^8$, $R^1$, $R^2$ and $R^3$ are the same or different, and are hydrogen atom, $C_{1-6}$ alkyl, $C_{1-6}$ alkoxy, $C_{2-7}$ car-bonylalkoxy or phenyl, or $R^3$ is as defined above and $R^1$ together with $R^2$ forms phenyl optionally substituted with two $C_{1-6}$ alkyls, $C_{1-6}$ alkoxys, $C_{2-7}$ carbonylalkoxys, and $R^7$ and $R^8$ are independently hydrogen atom or $C_{1-6}$ alkyl, or they together with the adjacent nitrogen atom form pyrrolidino, piperidino or homopiperidino, and, the following specific compound:

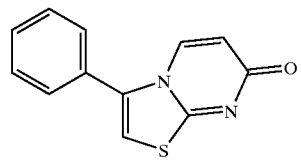

(GB 1345148)

3) As agrochemicals,

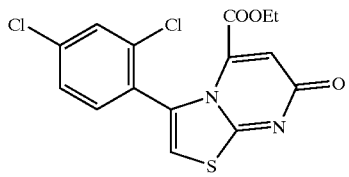

(Journal of Agricultural and Food Chemistry, 39 (12), 2300–2303 (1991))

4)

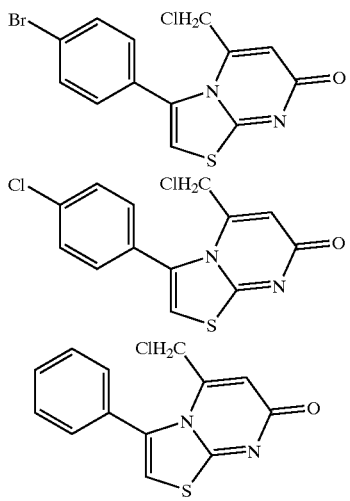

(Journal für Praktische Chemie, 330 (4) 607–616 (1991))

5)

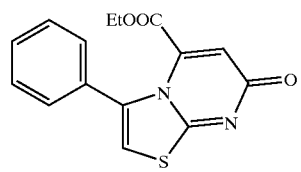

-continued

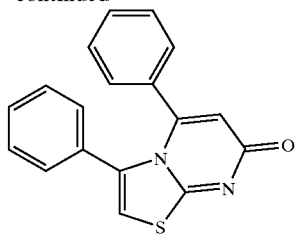
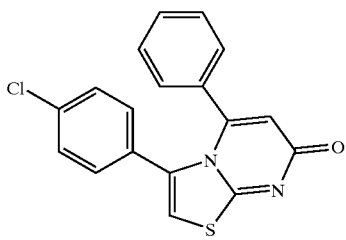
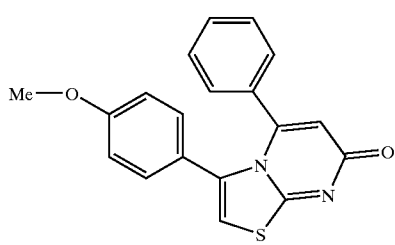
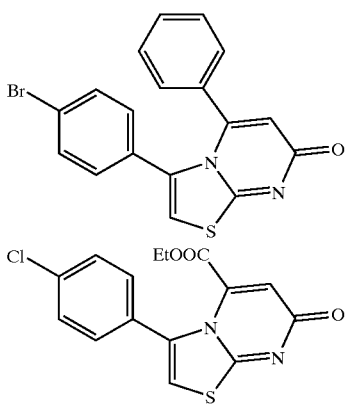
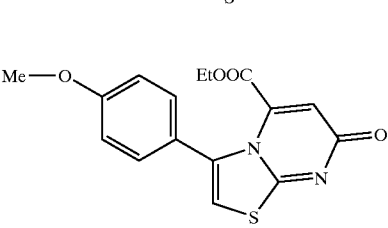
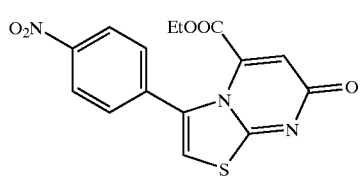

(Indian Journal of Chemistry, Section B, 23 B (2), 117–120 (1984))

6)

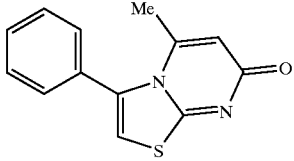

(Heterocyclics, 20 (6), 1089–1097 (1983))

7) As a compound having anti-microbial activity,

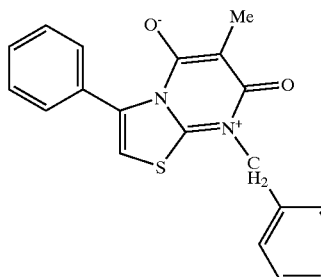

(Journal of Pharmaceutical Sciences, 62 (11), 1785–1789 (1973))

It is thought that adenosine causes asthma through its binding to an adenosine $A_3$ receptor, therefore $A_3$ adenosine receptor antagonists are expected to become a new type of anti-asthma drug and the like. Accordingly, an agent for antagonizing adenosine at adenosine $A_3$ receptors which has potent antagonistic activity, good oral absorption and good metabolical stability are expected to have potent therapeutic effects for asthma, inflammation, Addison's diseases, autoimmune hemolytic anemia, Crohn's diseases, psoriasis, rheumatism, central nerve diseases (e.g., cerebrovacular disorders such as haemorrhagia cerebri, cerebral infarction, etc., head injury, spinal injury, cerebral edema, etc.), diabetes and the like. However, as a prophylactic and therapeutic agent for adenosine $A_3$ receptor-related diseases, no good agent for antagonising adenosine at adenosine $A_3$ receptors are known in terms of potency, safety, bioavailability, metabolic stability, and the like. Therefore, a good agent for antagonising adenosine at adenosine $A_3$ receptors is expected to be developed.

DISCLOSURE OF THE INVENTION

As a result of the present inventors' intensive study, a compound represented by the formula (I):

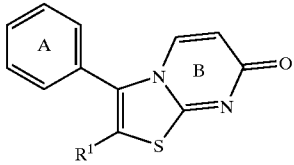

wherein ring A is an optionally substituted benzene ring, ring B may further be substituted, and $R^1$ is an optionally substituted cyclic group, or a salt thereof [hereinafter sometimes abbreviated to compound (I)], whose chemical structure is characterized in that the 2-position of the thiazolopyrimidine ring is substituted with an optionally substituted cyclic group and the 3-position thereof is substituted with an optionally substituted benzene ring, has been synthesized for the first time, and it has been found that the resultant compound (I) has an unexpected, excellent selective affinity to adenosine A_3 receptor and antagonistic activity at an adenosine A_3 receptor and high stability suitable for a medicine, due to its specific chemical structure, and it is therefore satisfactory as a medicine. Further, the present inventors have also found that a compound represented by the formula (Ia):

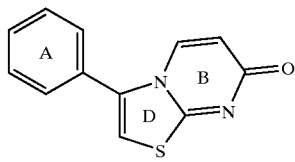

wherein ring A is an optionally substituted benzene ring, ring B may further be substituted, and ring D may further be substituted, provided that the, when the 5-position of the thiazolopyrimidine ring (ring B) is substituted by amino, the 2 position thereof (ring D) is substituted, or a salt thereof [hereinafter sometimes abbreviated to compound (Ia)] including compound (I) has an unexpected, excellent selective affinity to adenosine $A_3$ receptor and antagonistic activity at an adenosine $A_3$ receptor. On the basis of these findings, the inventors have completed the present invention.

That is, the present invention relates to:
1. A compound represented by the formula:

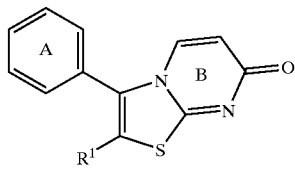

wherein ring A is an optionally substituted benzene ring, ring B may be further substituted, and $R^1$ is an optionally substituted cyclic group, or a salt thereof;

2. The compound according to the above 1, wherein ring A is benzene ring which may have 1 to 5 substituents selected from the group consisting of (i) halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) carboxy $C_{1-6}$ alkyl, (viii) carboxy $C_{2-6}$ alkenyl, (ix) optionally halogenated $C_{2-6}$ alkynyl, (x) optionally halogenated $C_{3-6}$ cycloalkyl, (xi) $C_{6-14}$ aryl, (xii) optionally halogenated $C_{1-6}$ alkoxy, (xiii) $C_{1-6}$ alkoxy-carbonyl-$C_{1-6}$ alkoxy, (xiv) hydroxy, (xv) $C_{6-14}$ aryloxy, (xvi) $C_{7-16}$ aralkyloxy, (xvii) mercapto, (xviii) optionally halogenated $C_{1-6}$ alkylthio, (xix) $C_{6-14}$ arylthio, (xx) $C_{7-16}$ aralkylthio, (xxi) amino, (xxii) mono-$C_{1-6}$ alkylamino, (xxiii) mono-$C_{6-14}$ arylamino, (xxiv) mono-$C_{7-16}$ aralkylamino, (xxv) di-$C_{7-16}$ aralkylamino, (xxvi) di-$C_{1-6}$ alkylamino, (xxvii) di-$C_{6-14}$ arylamino, (xxviii) formyl, (xxix) carboxy, (xxx) $C_{1-6}$ alkyl-carbonyl, (xxxi) $C_{3-6}$ cycloalkyl-carbonyl, (xxxii) $C_{1-6}$ alkoxy-carbonyl, (xxxiii) $C_{6-14}$ aryl-carbonyl, (xxxiv) $C_{7-16}$ aralkyl-carbonyl, (xxxv) $C_{6-14}$ aryloxy-carbonyl, (xxxvi) $C_{7-16}$ aralkyloxy-carbonyl, (xxxvii) 5- or 6-membered heterocyclic-carbonyl which contains, in addition to carbon atoms, 1 to 3 hetero atoms selected from nitrogen atom, oxygen atom and sulfur atom, (xxxviii) carbamoyl, (xxxix) thiocarbamoyl, (xxxx) mono-$C_{1-6}$ alkyl-carbamoyl, (xxxxi) di-$C_{1-6}$ alkyl-carbamoyl, (xxxxii) $C_{6-14}$ aryl-carbamoyl, (xxxxiii) 5- or 6-membered heterocyclic-carbamoyl which contains, in addition to carbon atoms, 1 to 3 hetero atoms selected from nitrogen atom, oxygen atom and sulfur atom, (xxxxiv) $C_{1-6}$ alkylsulfonyl, (xxxxv) $C_{6-14}$ arylsulfonyl, (xxxxvi) formylamino, (xxxxvii) $C_{1-6}$ alkyl-carbonylamino, (xxxxviii) $C_{6-14}$ aryl-carbonylamino, (xxxxix) $C_{1-6}$ alkoxy-carbonylamino, (xxxxx) $C_{1-6}$ alkylsulfonylamino, (xxxxxi) $C_{6-14}$ arylsulfonylamino, (xxxxxii) $C_{1-6}$ alkyl-carbonyloxy, (xxxxxiii) $C_{6-14}$ aryl-carbonyloxy, (xxxxxiv) $C_{1-6}$ alkoxy-carbonyloxy, (xxxxxv) mono-$C_{1-6}$ alkyl-carbamoyloxy, (xxxxxvi) di-$C_{1-6}$ alkyl-carbamoyloxy, (xxxxxvii) $C_{6-14}$ aryl-carbamoyloxy, (xxxxxviii) nicotinoyloxy, (xxxxxix) 5- to 7-membered saturated cyclic amino which may be substituted by a substituent selected from the group consisting of $C_{1-6}$ alkyl, $C_{6-14}$ aryl, $C_{1-6}$ alkyl-carbonyl, 5- to 10-membered aromatic heterocyclic group which contains, in addition to carbon atoms, 1 to 3 hetero atoms selected from nitrogen atom, oxygen atom and sulfur atom, and oxo, (xxxxxx) 5- to 10-membered aromatic heterocyclic group which contains, in addition to carbon atoms, 1 to 4 hetero atoms selected from nitrogen atom, oxygen atom and sulfur atom, and (xxxxxxi) sulfo (hereinafter referred to as C group-substituents), ring B may further have 1 or 2 substituents selected from the C group substituents, and $R^1$ is $C_{3-6}$ cycloalkyl group, $C_{1-14}$ aryl group or a monovalent group formed by removing any one hydrogen atom from 5- to 14-membered heterocyclic ring which contains, in addition to carbon atom(s), 1 to 4 hetero atoms selected from nitrogen atom, sulfur atom and oxygen atom, each of which may have 1 to 5 substituents selected from the C group substituents;

3. The compound according to the above 2, wherein $R^1$ is a monovalent group formed by removing any one hydrogen atom from 5- to 14-membered heterocyclic ring which contains, in addition to carbon atom(s), 1 to 4 hetero atoms selected from nitrogen atom, sulfur atom and oxygen atom, and which may have 1 to 5 substituents selected from the C group substituents as defined in the above 2;

4. The compound according to the above 2 or 3, wherein the 5- to 14-membered heterocyclic ring is (i) 5- to 14-membered aromatic heterocyclic ring selected from the group consisting of thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan and phenoxazine, or a ring formed by this ring fused to one or two benzene rings, (ii) 5- to 10-membered aliphatic heterocyclic ring selected from the group consisting of pyrrolidine, imidazoline, pyrazolidine, pyrazoline, piperidine, piperazine, morpholine, thiomorpholine, dioxazole, oxadiazoline, thiadiazoline, triazoline, thiadiazole and dithiazole, or (iii) 7- to 10-membered bridged heterocyclic ring selected from the group consisting of quinuclidine and 7-azabicyclo[2.2.1]heptane;

5. The compound according to the above 2 or 3, wherein the monovalent group formed by removing any one hydrogen atom from the 5- to 14-membered heterocyclic ring is 5- to 14-membered nitrogen-containing aromatic heterocyclic group which contains, in addition to carbon atom(s), 1 to 4 hetero atoms selected from the group consisting of nitrogen atom, sulfur atom and oxygen atom;

6. The compound according to the above 2 or 3, wherein the monovalent group formed by removing any one hydrogen atom from 5- to 14-membered heterocyclic ring is 2-pyridyl group, 3-pyridyl group, 4-pyridyl group, 2-quinolyl group, 3-quinolyl group, 4-quinolyl group, 5-quinolyl group, 8-quinolyl group, 1-isoquinolyl group, 3-isoquinolyl group, 4-isoquinolyl group, 5-isoquinolyl group, pyrazinyl group, 2-pyrimidinyl group, 4-pyrimidinyl group, 3-pyrrolyl group, 2-imidazolyl group, 3-pyridazinyl group, 3-isothiazolyl group, 3-isoxazolyl group, 1-indolyl group, 2-indolyl group, 3-indolyl group or 2-benzothiazolyl group;

7. The compound according to the above 2 or 3, wherein the monovalent group formed by removing any one hydrogen atom from 5- to 14-membered heterocyclic ring is 5- or 6-membered nitrogen-containing aromatic heterocyclic group which contains, in addition to carbon atoms, 1 to 3 hetero atoms selected from nitrogen atom, sulfur atom and oxygen atom;

8. The compound according to the above 2 or 3, wherein the monovalent group formed by removing any one hydrogen atom from 5- to 14-membered heterocyclic ring is 2-pyridyl group, 3-pyridyl group, 4-pyridyl group, pyrazinyl group, 2-pyrimidinyl group, 4-pyrimidinyl group, 3-pyrrolyl group, 3-pyridazinyl group, 3-isothiazolyl group or 3-isoxazolyl group.

9. The compound according to the above 2 or 3, wherein the monovalent group formed by removing any one hydrogen atom from 5- to 14-membered heterocyclic ring is pyridyl group;

10. The compound according to the above 1, wherein $R^1$ is 4-pyridyl group;

11. The compound according to the above 1, wherein $R^1$ is an optionally substituted nitrogen-containing aromatic heterocyclic group;

12. The compound according to the above 1, wherein ring A is benzene ring which may be substituted with $C_{1-6}$ alkoxy, or one or two $C_{1-6}$ alkyls;

13. The compound according to the above 1, wherein ring A is benzene ring which may be substituted with $C_{1-6}$ alkoxy;

14. The compound according to the above 1, wherein the substituent by which ring B may further be substituted is amino;

15. The compound according to the above 1, wherein ring A is benzene ring which may be substituted with $C_{1-6}$ alkoxy, or one or two $C_{1-6}$ alkyls, ring B may further be substituted with amino and $R^1$ is pyridyl group;

16. The compound according to the above 1, wherein ring A is benzene ring which may be substituted with $C_{1-6}$ alkoxy, ring B may further be substituted with amino and $R^1$ is pyridyl group;

17. The compound according to the above 1 which is represented by the formula:

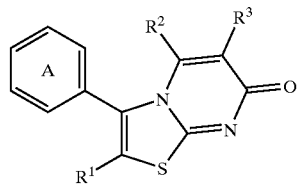

wherein $R^2$ and $R^3$ are the same or different, and are hydrogen atom or a substituent selected from the C group substituents, and ring A and $R^1$ are as defined in the above 1, or a salt thereof;

18. The compound according to the above 17, wherein $R^3$ is hydrogen atom;

19. (1) 5-amino-3-(4-methoxyphenyl)-2-(4-pyridyl)-7H-thiazolo[3,2-a]pyrimidin-7-one or its salt, (2) 5-amino-3-[4-(1,1-dimethylethyl)phenyl]-2-(4-pyridyl)-7H-thiazolo[3,2-a]pyrimidin-7-one or its salt, or (3) 5-amino-3-(3,5-dimethylphenyl)-2-(4-pyridyl)-7H-thiazolo[3,2-a]pyrimidin-7-one or its salt;

20. A prodrug of the compound according to the above 1;

21. A process for producing the compound according to the above 1 or a salt thereof which comprises reacting a compound represented by the formula:

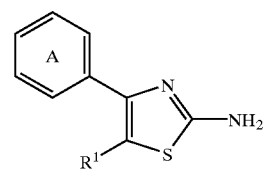

wherein each symbol is as defined above 1, or its salt, with a compound represented by the formula:

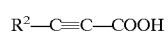

wherein $R^2$ is as defined in the above 1, or its salt or reactive derivative, or a compound represented by the formula:

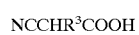

wherein $R^3$ is as defined in the above 1, or its salt or reactive derivative;

22. A pharmaceutical composition comprising a compound represented by the formula:

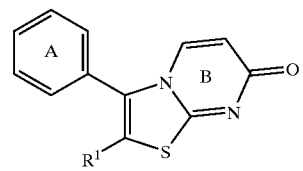

wherein ring A is an optionally substituted benzene ring, ring B may further be substituted, and $R^1$ is an optionally substituted cyclic group, or a salt or a prodrug thereof;

23. The composition according to the above 22 which is an adenosine $A_3$ receptor antagonist;

24. The composition according to the above 22 which is an agent for preventing and/or treating diseases related to adenosine $A_3$ receptors;

25. The composition according to the above 22 which is an agent for preventing and/or treating asthma or allergic disease;

26. The composition according to the above 22 which is an agent for preventing and/or treating cerebrovascular disorders;

27. The composition according to the above 22 which is an agent for preventing and/or treating head injury;

28. The composition according to the above 22 which is an agent for preventing and/or treating cerebral edema;

29. An adenosine $A_3$ receptor antagonist comprising a compound represented by the formula:

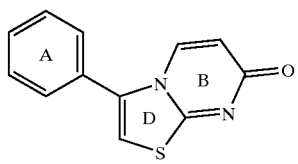

wherein ring A is an optionally substituted benzene ring, ring B may further be substituted, and ring D may further be substituted, provided that, when the 5-position of thiazolopyrimidine ring is substituted with amino, the 2-position thereof is substituted, or a salt thereof;

30. The antagonist according to the above 29, wherein ring A is benzene ring which may have 1 to 5 substituents selected from the group consisting of (i) halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) carboxy $C_{1-6}$ alkyl, (viii) carboxy $C_{2-6}$ alkenyl, (ix) optionally halogenated $C_{2-6}$ alkynyl, (x) optionally halogenated $C_{3-6}$ cycloalkyl, (xi) $C_{6-14}$ aryl, (xii) optionally halogenated $C_{1-6}$ alkoxy, (xiii) $C_{1-6}$ alkoxy-carbonyl-$C_{1-6}$ alkoxy, (xiv) hydroxy, (xv) $C_{6-14}$ aryloxy, (xvi) $C_{7-16}$ aralkyloxy, (xvii) mercapto, (xviii) optionally halogenated $C_{1-6}$ alkylthio, (xix) $C_{6-14}$ arylthio, (xx) $C_{7-16}$ aralkylthio, (xxi) amino, (xxii) mono-$C_{1-6}$ alkylamino, (xxiii) mono-$C_{6-14}$ arylamino, (xxiv) mono-$C_{7-16}$ aralkylamino, (xxv) di-$C_{7-16}$ aralkylamino, (xxvi) di-$C_{1-6}$ alkylamino, (xxvii) di-$C_{6-14}$ arylamino, (xxviii) formyl, (xxix) carboxy, (xxx) $C_{1-6}$ alkyl-carbonyl, (xxxi) $C_{3-6}$ cycloalkyl-carbonyl, (xxxii) $C_{1-6}$ alkoxy-carbonyl, (xxxiii) $C_{6-14}$ aryl-carbonyl, (xxxiv) $C_{7-16}$ aralkyl-carbonyl, (xxxv) $C_{6-14}$ aryloxy-carbonyl, (xxxvi) $C_{7-16}$ aralkyloxy-carbonyl, (xxxvii) 5- or 6-membered heterocyclic-carbonyl which contains, in addition to carbon atoms, 1 to 3 hetero atoms selected from nitrogen atom, oxygen atom and sulfur atom, (xxxviii) carbamoyl, (xxxix) thiocarbamoyl, (xxxx) mono-$C_{1-6}$ alkyl-carbamoyl, (xxxxi) di-$C_{1-6}$ alkyl-carbamoyl, (xxxxii) $C_{6-14}$ aryl-carbamoyl, (xxxxiii) 5- or 6-membered heterocyclic-carbamoyl which contains, in addition to carbon atoms, 1 to 3 hetero atoms selected from nitrogen atom, oxygen atom and sulfur atom, (xxxxiv) $C_{1-6}$ alkylsulfonyl, (xxxxv) $C_{6-14}$ arylsulfonyl, (xxxxvi) formylamino, (xxxxvii) $C_{1-6}$ alkyl-carbonylamino, (xxxxviii) $C_{6-14}$ aryl-carbonylamino, (xxxxix) $C_{1-6}$ alkoxy-carbonylamino, (xxxxx) $C_{1-6}$ alkylsulfonylamino, (xxxxxi) $C_{6-14}$ arylsulfonylamino, (xxxxxii) $C_{1-6}$ alkyl-carbonyloxy, (xxxxxiii) $C_{6-14}$ aryl-carbonyloxy, (xxxxxiv) $C_{1-6}$ alkoxy-carbonyloxy, (xxxxxv) mono-$C_{1-6}$ alkyl-carbamoyloxy, (xxxxxvi) di-$C_{1-6}$ alkyl-carbamoyloxy, (xxxxxvii) $C_{6-14}$ aryl-carbamoyloxy, (xxxxxviii) nicotinoyloxy, (xxxxxix) 5- to 7-membered saturated cyclic amino which may be substituted by a substituent selected from the group consisting of $C_{1-6}$ alkyl, $C_{6-14}$ aryl, $C_{1-6}$ alkyl-carbonyl, 5- to 10-membered aromatic heterocyclic group which contains, in addition to carbon atoms, 1 to 3 hetero atoms selected from nitrogen atom, oxygen atom and sulfur atom, and oxo, (xxxxxx) 5- to 10-membered aromatic heterocyclic group which contains, in addition to one nitrogen atom and carbon atoms, 1 to 4 hetero atoms selected from nitrogen atom, oxygen atom and sulfur atom, and (xxxxxxi) sulfo (hereinafter referred to as C group substituents), ring B may further have 1 or 2 substituents selected from the C group substituents, and ring D may further have a substituent selected from the C group substituents;

31. A method for antagonizing adenosine $A_3$ receptors which comprises administrating to a mammal an effective amount of a compound represented by the formula:

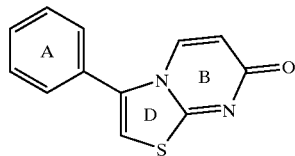

wherein ring A is an optionally substituted benzene ring, ring B may further be substituted, and ring D may further be substituted, provided that, when the 5-position of thiazolopyrimidine ring is substituted with amino, the 2-position thereof is substituted, or its salt or its prodrug;

32. A method for preventing and/or treating asthma, allergic disease, cerebrovascular disorders, head injury or cerebral edema which comprises administrating to a mammal an effective amount of a compound represented by the formula:

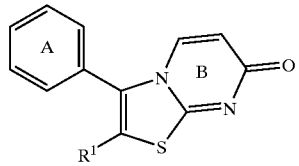

wherein ring A is an optionally substituted benzene ring, is ring B may further be substituted, and $R^1$ is an optionally substituted cyclic group, or its salt or its prodrug;

33. Use of a compound represented by the formula:

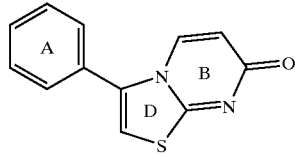

wherein ring A is an optionally substituted benzene ring, ring B may further be substituted, and ring D may further be substituted, provided that, when the 5-position of thiazolopyrimidine ring is substituted with amino, the 2-position thereof is substituted, or its salt or its prodrug, for manufacturing an adenosine $A_3$ receptor antagonist; and 34. Use of a compound represented by the formula:

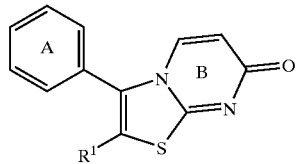

wherein ring A is an optionally substituted benzene ring, ring B may further be substituted, and $R^1$ is an optionally substituted cyclic ring, or its salt or its prodrug, for manufacturing an agent for preventing and/or treating asthma, allergic disease, cerebrovascular disorders, head injury or cerebral edema.

Further, the present invention relates to:
35. A compound represented by the formula:

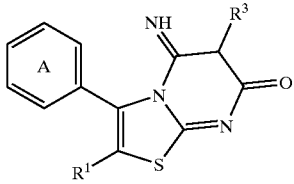

wherein $R^3$ is a substituent, ring A is an optionally substituted benzene ring, and $R^1$ is an optionally substituted cyclic group, or a salt thereof; and 36. An adenosine $A_3$ receptor antagonist comprising a compound represented by the formula:

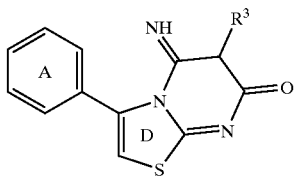

wherein $R^3$ is a substituent, ring A is an optionally substituted benzene ring, and ring D may further be substituted, or a salt thereof.

BEST EMBODIMENT OF THE INVENTION

In the above formulas, ring A is an optionally substituted benzene ring.

Examples of the optional "substituent" of ring A include halogen atom (e.g., fluorine, chlorine, bromine, iodine, etc.), $C_{1-3}$ alkylenedioxy (e.g., methylenedioxy, ethylenedioxy, etc.) nitro, cyano, optionally halogenated $C_{1-6}$ alkyl, optionally halogenated $C_{2-6}$ alkenyl, carboxy $C_{1-6}$ alkyl (e.g., carboxymethyl, carboxyethyl, etc.), carboxy $C_{2-6}$ alkenyl (e.g., 2-carboxyethenyl, 2-carboxy-2-methylethenyl, etc.), optionally halogenated $C_{2-6}$ alkynyl, optionally halogenated $C_{3-6}$ cycloalkyl, $C_{6-14}$ aryl (e.g., phenyl, 1-naphthyl, 2-naphthyl, 2-biphenylyl, 3-biphenylyl, 4-biphenylyl, 2-anthryl, etc.), optionally halogenated $C_{1-6}$ alkoxy, $C_{1-6}$ alkoxy-carbonyl-$C_{1-6}$ alkoxy (e.g., ethoxycarbonylmethyloxy, etc.), hydroxy, $C_{6-14}$ aryloxy (e.g., phenyloxy, 1-naphthyloxy, 2-naphthyloxy, etc.), $C_{7-16}$ aralkyloxy (e.g., benzyloxy, phenethyloxy, etc.), mercapto, optionally halogenated $C_{1-6}$ alkylthio, $C_{6-14}$ arylthio (e.g., phenylthio, 1-naphthylthio, 2-naphthylthio, etc.), $C_{7-16}$ aralkylthio (e.g., benzylthio, phenethylthio, etc.), amino, mono-$C_{1-6}$ alkylamino (e.g., methylamino, ethylamino, etc.), mono-$C_{6-14}$ arylamino (e.g., phenylamino, 1-naphthylamino, 2-naphthylamino, etc.), mono-$C_{7-16}$ aralkylamino (e.g., benzylamino, phenethylamino, etc.), di-$C_{7-16}$ aralkylamino (e.g., dibenzylamino, diphenethylamino, etc.), di-$C_{1-6}$ alkylamino (e.g., dimethylamino, diethylamino, ethylmethylamino, etc.), di-$C_{6-14}$ arylamino (e.g., diphenylamino, etc.), formyl, carboxy, $C_{1-6}$ alkyl-carbonyl (e.g., acetyl, propionyl, etc.), $C_{3-6}$ cycloalkyl-carbonyl (e.g., cyclopropylcarbonyl, cyclopentylcarbonyl, cyclohexylcarbonyl, etc.), $C_{1-6}$ alkoxy-carbonyl (e.g., methoxycarbonyl, ethoxycarbonyl, propoxycarbonyl, tert-butoxycarbonyl, etc.), $C_{6-14}$ aryl-carbonyl (e.g., benzoyl, 1-naphthoyl, 2-naphthoyl, etc.), $C_{7-16}$ aralkyl-carbonyl (e.g., phenylacetyl, 3-phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, phenethyloxycarbonyl, etc.), 5- or 6-membered heterocyclic-carbonyl which contains, in addition to carbon atoms, 1 to 3 hetero atoms selected from nitrogen atom, oxygen atom and sulfur atom (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), carbamoyl, thiocarbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-14}$ aryl-carbamoyl (e.g., phenylcarbamoyl, 1-naphthylcarbamoyl, 2-naphthylcarbamoyl, etc.), 5- or 6-membered heterocyclic-carbamoyl which contains, in addition to carbon atoms, 1 to 3 hetero atoms selected from nitrogen atom, oxygen atom and sulfur atom (e.g., 2-pyridylcarbamoyl, 3-pyridylcarbamoyl, 4-pyridylcarbamoyl, 2-thienylcarbamoyl, 3-thienylcarbamoyl, etc.), $C_{1-6}$ alkylsulfonyl (e.g., methylsulfonyl, ethylsulfonyl, etc.), $C_{6-14}$ arylsulfonyl (e.g., phenylsulfonyl, 1-naphthylsulfonyl, 2-naphthylsulfonyl, etc.), formylamino, $C_{1-6}$ alkyl-carbonylamino (e.g., acetylamino, etc.), $C_{6-14}$ aryl-carbonylamino (e.g., benzoylamino, naphthoylamino, etc.), $C_{1-6}$ alkoxy-carbonylamino (e.g., methoxycarbonylamino, ethoxycarbonylamino, propoxycarbonylamino, butoxycarbonylamino, etc.), $C_{1-6}$ alkylsulfonylamino (e.g., methylsulfonylamino, ethylsulfonylamino, etc.), $C_{6-14}$ arylsulfonylamino (e.g., phenylsulfonylamino, 2-naphthylsulfonylamino, 1-naphthylsulfonylamino, etc.), $C_{1-6}$ alkyl-carbonyloxy (e.g., acetoxy, propionyloxy, etc.), $C_{6-14}$ aryl-carbonyloxy (e.g., benzoyloxy, naphthylcarbonyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ehtylcarbamoyloxy, etc.), di-$C_{1-6}$ alkyl-carbamoyloxy (dimethylcarbamoyloxy, diethylcarbamoyloxy, etc.), $C_{6-14}$ aryl-carbamoyloxy (e.g., phenylcarbamoyloxy, naphthylcarbamoyloxy, etc.), nicotinoyloxy, 5- to 7-membered saturated cyclic amino which may be substituted, 5- to 10-membered aromatic heterocyclic group which contains, in addition to carbon atoms, 1 to 4 hetero atoms selected from nitrogen atom, oxygen atom and sulfur atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), sulfo and the like (hereinafter sometimes referred to as C group substituents).

Ring A may have 1 to 5, preferably 1 to 3, more preferably 1 or 2 substituents as mentioned above at possible positions thereof and, when the number of substituents is two or more, those substituents may be the same as or different from one another.

The above-mentioned "optionally halogenated $C_{1-6}$ alkyl" includes, for example, $C_{1-6}$ alkyl (e.g., methyl, ethyl, propyl, isopropyl, butyl, isobutyl, sec-butyl, tert-butyl, pentyl, hexyl, etc.) which may have 1 to 5, preferably 1 to 3 halogen atoms (e.g., fluorine, chlorine, bromine, iodine, etc.). Specific examples thereof include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

The above-mentioned "optionally halogenated $C_{2-6}$ alkenyl" includes, for example, $C_{2-6}$ alkenyl (e.g., vinyl, propenyl, isopropenyl, 2-buten-1-yl, 4-penten-1-yl, 5-hexen-1-yl, etc.) which may have 1 to 5, preferably 1 to 3 halogen atoms (e.g., fluorine, chlorine, bromine, iodine, etc.) and the like.

The above-mentioned "optionally halogenated $C_{2-6}$ alkynyl" includes, for example, $C_{2-6}$ alkynyl (e.g., 2-butyn-1-yl, 4-pentyn-1-yl, 5-hexyn-1-yl, etc.) which may have 1 to 5, preferably 1 to 3 halogen atoms (e.g., fluorine, chlorine, bromine, iodine, etc.), and the like.

The above-mentioned "optionally halogenated $C_{3-6}$ cycloalkyl" includes, for example, $C_{3-6}$ cycloalkyl (e.g., cyclopropyl, cyclobutyl, cyclopentyl, cyclohexyl, etc.) which may have 1 to 5, preferably 1 to 3 halogen atoms (e.g., fluorine, chlorine, bromine, iodine, etc.). Specific examples thereof include cyclopropyl, cyclobutyl, cyclopentyl, cyclohexyl, 4,4-dichlorocyclohexyl, 2,2,3,3-tetrafluorocyclopentyl, 4-chlorocyclohexyl, etc.

The above-mentioned "optionally halogenated $C_{1-6}$ alkoxy" includes, for example, $C_{1-6}$ alkoxy (e.g., methoxy, ethoxy, propoxy, isopropoxy, butoxy, isobutoxy, sec-butoxy, pentyloxy, hexyloxy, etc.) which may have 1 to 5, preferably 1 to 3 halogen atoms (e.g., fluorine, chlorine, bromine, iodine, etc.). Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc., and preferably methoxy, etc.

The above-mentioned "optionally halogenated $C_{1-6}$ alkylthio" includes, for example, $C_{1-6}$ alkylthio (e.g., methylthio, ethylthio, propylthio, isopropylthio, butylthio, sec-butylthio, tert-butylthio, etc.) which may have 1 to 5, preferably 1 to 3 halogen atoms (e.g., fluorine, chlorine, bromine, iodine, etc.). Specific examples thereof include methylthio, difluoromethylthio, trifluoromethylthio, ethylthio, propylthio, isopropylthio, butylthio, 4,4,4-trifluorobutylthio, pentylthio, hexylthio, etc.

The above-mentioned "5- to 7-membered saturated cyclic amino" of the "5- to 7-membered saturated cyclic amino which may be substituted" includes, for example, 5- to 7-membered saturated cyclic amino optionally containing 1 to 4 hetero atoms of 1 or 2 species selected from the group consisting of nitrogen, sulfur and oxygen atoms in addition to carbon atoms and at least one nitrogen atom. Specific examples thereof include pyrrolidin-1-yl, piperidino, piperazin-1-yl, morpholino, thiomorpholino, tetrahydroazepin-1-yl, etc.

The "substituents" of the "5- to 7-membered saturated cyclic amino which may be substituted" include, for example, 1 to 3 substituents selected from the group consisting of $C_{1-6}$ alkyl (e.g., methyl, ethyl, propyl, isopropyl, butyl, isobutyl, sec-butyl, tert-butyl, pentyl, hexyl, etc.), $C_{6-14}$ aryl (e.g., phenyl, 1-naphthyl, 2-naphthyl, 2-biphenylyl, 3-biphenylyl, 4-biphenylyl, 2-anthryl, etc.), $C_{1-6}$ alkyl-carbonyl (e.g., acetyl, propionyl, etc.), and 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), oxo, and the like.

Among the above substituents, optionally halogenated $C_{1-6}$ alkoxy and one or two optionally halogenated $C_{1-6}$ alkyls are preferred. In particular, $C_{1-6}$ alkoxy and one to two $C_{1-6}$ alkyls are preferred, with two methyls, one tert-butyl, one methoxy, etc. being most preferred.

In the above formulas, ring B may further be substituted.

The optional "substituent(s)" of ring B are, for example, the same as the optional substituent(s) of ring C (the C group substituents) and the like.

As the optional "substituent(s)" of ring B, among others, preferred are groups other than $C_{1-6}$ alkoxy-carbonyl, for example, halogen atom (e.g., fluorine, chlorine, bromine, iodine, etc.), $C_{1-3}$ alkylenedioxy (e.g., methylenedioxy, ethylenedioxy, etc.) nitro, cyano, optionally halogenated $C_{1-6}$ alkyl, optionally halogenated $C_{2-6}$ alkenyl, carboxy $C_{2-6}$ alkenyl (e.g., 2-carboxyethenyl, 2-carboxy-2-methylethenyl, etc.), optionally halogenated $C_{2-6}$ alkynyl, optionally halogenated $C_{3-6}$ cycloalkyl, $C_{6-14}$ aryl (e.g., phenyl, 1-naphthyl, 2-naphthyl, 2-biphenylyl, 3-biphenylyl, 4-biphenylyl, 2-anthryl, etc.), optionally halogenated $C_{1-6}$ alkoxy, $C_{1-6}$ alkoxy-carbonyl-$C_{1-6}$ alkoxy (e.g., ethoxycarbonylmethyloxy, etc.), hydroxy, $C_{6-14}$ aryloxy (e.g., phenyloxy, 1-naphthyloxy, 2-naphthyloxy, etc.), $C_{7-16}$ aralkyloxy (e.g., benzyloxy, phenethyloxy, etc.), mercapto, optionally halogenated $C_{1-6}$ alkylthio, $C_{6-14}$ arylthio (e.g., phenylthio, 1-naphthylthio, 2-naphthylthio, etc.), $C_{7-16}$ aralkylthio (e.g., benzylthio, phenethylthio, etc.), amino, mono-$C_{1-6}$ alkylamino (e.g., methylamino, ethylamino, etc.), mono-$C_{6-14}$ arylamino (e.g., phenylamino, 1-naphthylamino, 2-naphthylamino, etc.), di-$C_{1-6}$ alkylamino (e.g., dimethylamino, diethylamino, ethylmethylamino, etc.), di-$C_{6-14}$ arylamino (e.g., diphenylamino, etc.), mono-$C_{7-16}$ aralkylamino (e.g., benzylamino, phenethylamino, etc.), di-$C_{7-16}$ aralkylamino (e.g., dibenzylamino, diphenethylamino, etc.), formyl, carboxy, $C_{1-6}$ alkyl-carbonyl (e.g., acetyl, propionyl, etc.), $C_{3-6}$ cycloalkyl-carbonyl (e.g., cyclopropylcarbonyl, cyclopentylcarbonyl, cyclohexylcarbonyl, etc.), $C_{6-14}$ arylcarbonyl (e.g., benzoyl, 1-naphthoyl, 2-naphthoyl, etc.), $C_{7-16}$ aralkyl-carbonyl (e.g., phenylacetyl, 3-phenylpropionyl, etc.), $C_{6-14}$ aryloxy-carbonyl (e.g., phenoxycarbonyl, etc.), $C_{7-16}$ aralkyloxy-carbonyl (e.g., benzyloxycarbonyl, phenethyloxycarbonyl, etc.), 5- or 6-membered heterocyclic-carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), carbamoyl, thiocarbamoyl, mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, ethylmethylcarbamoyl, etc.), $C_{6-14}$ aryl-carbamoyl (e.g., phenylcarbamoyl, 1-naphthylcarbamoyl, 2-naphthylcarbamoyl, etc.), 5- or 6-membered heterocyclic-carbamoyl (e.g., 2-pyridylcarbamoyl, 3-pyridylcarbamoyl, 4-pyridylcarbamoyl, 2-thienylcarbamoyl, 3-thienylcarbamoyl, etc.), $C_{1-6}$ alkylsulfonyl (e.g., methylsulfonyl, ethylsulfonyl, etc.), $C_{6-14}$ arylsulfonyl (e.g., phenylsulfonyl, 1-naphthylsulfonyl, 2-naphthylsulfonyl, etc.), formylamino, $C_{1-6}$ alkyl-carbonylamino (e.g., acetylamino, etc.), $C_{6-14}$ aryl-carbonylamino (e.g., benzoylamino, naphthoylamino, etc.), $C_{1-6}$ alkoxy-carbonylamino (e.g., methoxycarbonylamino, ethoxycarbonylamino, propoxycarbonylamino, butoxycarbonylamino, etc.), $C_{1-6}$ alkylsulfonylamino (e.g., methylsulfonylamino, ethylsulfonylamino, etc.), $C_{6-14}$ arylsulfonylamino (e.g., phenylsulfonylamino, 2-naphthylsulfonylamino, 1-naphthylsulfonylamino, etc.), $C_{1-6}$ alkyl-carbonyloxy (e.g., acetoxy, propionyloxy, etc.), $C_{6-14}$ aryl-carbonyloxy (e.g., benzoyloxy, naphthylcarbonyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (dimethylcarbamoyloxy, diethylcarbamoyloxy, etc.), $C_{6-14}$ aryl-carbamoyloxy (e.g., phenylcarbamoyloxy, naphthylcarbamoyloxy, etc.), nicotinoyloxy, 5- to 7-membered saturated cyclic amino which may be substituted, 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), sulfo and the like. In particular, amino and the like are preferred.

Ring B may have 1 or 2 substituents as mentioned above at possible positions thereof (5- or 6-position)), preferable one substituent at 5-position, and, when the number of substituents is two or more, those substituents may be the same as or different from one another.

In addition, the substituents at 5- and 6-position of ring B in the compounds (I) and (Ia) can be indicated as $R^2$ and $R^3$, respectively, as follows.

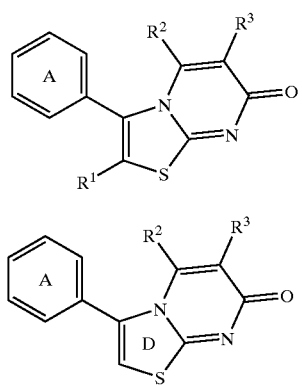

$R^2$ and $R^3$ may be any groups which can be present at 5- and 6-positions, respectively, and preferred examples include hydrogen atom and the like, in addition to the above-mentioned substituents of ring B. In particular, preferred $R^3$ is hydrogen atom and, as $R^2$, amino group is preferred.

In the above formulas, $R^1$ is a cyclic group which may be substituted.

The "cyclic group" of the "cyclic group which may be substituted" includes, for example, a cyclic hydrocarbon group, a heterocyclic group and the like.

Examples of the above-mentioned "cyclic hydrocarbon group" include cycloalkyl group, aryl group and the like. Among them, a cyclic hydrocarbon group having 1 to 16 carbon atoms is preferred.

As "cycloalkyl group", for example, $C_{3-6}$ cycloalkyl group (e.g., cyclopropyl, cyclobutyl, cyclopentyl, cyclohexyl, etc.) and the like are preferred.

As "aryl group", for example, $C_{6-14}$ aryl group (e.g., phenyl, 1-naphthyl, 2-naphthyl, 2-biphenylyl, 3-biphenylyl, 4-biphenylyl, 2-anthryl, etc.) and the like are preferred.

As the above-mentioned "heterocyclic group", there are, for example, a monovalent group formed by removing an optional hydrogen atom from a 5- to 14-membered (monocyclic, bicyclic or tricyclic) heterocyclic ring containing 1 to 4 hetero atoms of 1 or 2 species selected from the group consisting of nitrogen, sulfur and oxygen atoms in addition to carbon atoms, preferably, (i) a 5- to 14-membered, preferably, 5- to 10-membered aromatic heterocyclic ring, (ii) a 5- to 10-membered aliphatic heterocyclic ring and (iii) a 7- to 10-membered bridged heterocyclic ring, etc.

The above-mentioned "5- to 14-membered (preferably 5- to 10-membered) aromatic heterocyclic ring" includes, for example, an aromatic heterocyclic ring such as thiophene, benzo[b]thiophene, benzo[b]furan, benzimidazole, benzoxazole, benzothiazole, benzisothiazole, naphtho[2,3-]thiophene, furan, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine, etc.; and a ring as formed through condensation of those rings (preferably a monocyclic ring) with one or more (preferably one or two) aromatic rings (e.g., benzene ring, etc.), etc.

The above-mentioned "5- to 10-membered aliphatic heterocyclic ring" includes, for example, pyrrolidine, imidazoline, pyrazolidine, pyrazoline, piperidine, piperazine, morpholine, thiomorpholine, dioxazole, oxadiazoline, oxathiazole, thiadiazoline, triazoline, thiadiazole, dithiazole, etc.

The above-mentioned "7- to 10-membered bridged heterocyclic ring" includes, for example, quinuclidine, 7-azabicyclo[2.2.1]heptane, etc.

Preferable examples of the "heterocyclic group" include, for example, a 5- to 14-membered (preferably 5- to 10-membered) (monocyclic or bicyclic) heterocyclic group containing 1 to 4 hetero atoms of 1 or 2 species selected from the group consisting of nitrogen, sulfur and oxygen atoms in addition to carbon atoms (e.g., 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, etc.).

When the heterocyclic group contains nitrogen atom (N) or sulfur atom (S), N or S may be oxidized (N-oxide, S-oxide).

Among these groups, a nitrogen-containing 5- or 6-membered aromatic heterocyclic group containing 1 to 3 hetero atoms selected from the group consisting of nitrogen, sulfur and oxygen atoms in addition to carbon atoms (e.g., 2-pyridyl, 3-pyridyl, 4-pyridyl, pyrazinyl, 2-pyrimidinyl, 4-pyrimidinyl, 3-pyrrolyl, 3-pyridazinyl, 3-isothiazolyl, 3-isoxazolyl, etc.) and the like are preferred. For example, pyridyl (e.g., 2-pyridyl, 3-pyridyl, 4-pyridyl, in particular, 4-pyridyl, etc.) and the like are more preferred.

The "substituents" of the "cyclic group which may be substituted" are the same as those mentioned above for the "substituents" of ring A.

The "cyclic group" may have 1 to 5, preferably 1 to 3 substituents as mentioned above at possible positions of the cyclic group and, when the number of substituents is two or more, those substituents may be the same as or different from one another.

Further, for $R^1$, a basic group is preferred. As a basic group, pyridyl (e.g., 2-pyridyl, 3-pyridyl, 4-pyridyl), in particular, 4-pyridyl is preferred.

In the above formula, ring D may further be substituted.

The further optional "substituent(s)" of ring D are the same as those mentioned above for the optional substituent(s) of ring A (C group substituents). Preferably, the further optional substituent is the above $R^1$.

Preferred Example of Compound (Ia) is Compound (I).

Preferred example of compound (I) is that wherein $R^1$ is a nitrogen-containing aromatic heterocyclic group which may be substituted and ring B may have substituent(s) other than $C_{1-6}$ alkoxy-carbonyl.

More specifically, the followings are preferably used as compound (I):

(1) compound (I) wherein ring A is benzene ring which may be substituted with $C_{1-6}$ alkoxy or one or two $C_{1-6}$ alkyl, ring B may further have amino and $R^1$ is pyridyl group, or a salt thereof;

(2) compound (I) wherein ring A is benzene ring which may be substituted with $C_{1-6}$ alkoxy, ring B may further have amino and $R^1$ is pyridyl group, or a salt thereof;

(3) 1) 5-amino-3-(4-methoxyphenyl)-2-(4-pyridyl)-7H-thiazolo[3,2-a]pyrimidin-7-one, 2) 5-amino-3-[4-(1,1-dimethylethyl)phenyl]-2-(4-pyridyl)-7H-thiazolo[3,2-a]pyrimidin-7-one, 3) 5-amino-3-(3,5-dimethylphenyl)-2-(4-pyridyl)-7H-thiazolo[3,2-a]pyrimidin-7-one, or a salt thereof;

(4) 5-amino-3-(4-methoxyphenyl)-2-(4-pyridyl)-7H-thiazolo[3,2-a]pyrimidin-7-one or a salt thereof.

Salts of compound (I) and compound (Ia) include, for example, metal salts, ammonium salts, salts with organic bases, salts with inorganic acids, salts with organic acids, salts with basic or acidic amino acids, etc. Preferred examples of metal salts include alkali metal salts such as sodium salts, potassium salts; alkaline earth metal salts such as calcium salts, magnesium salts, barium salts; aluminum salts, etc. Preferred examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of salts with inorganic acids include hydrochlorides, hydrobromides, nitrates, sulfates, phosphates, etc. Preferred examples of salts with organic acids include formates, acetates, trifluoroacetates, phthalate, fumarates, oxalates, tartarates, maleates, citrates, succinates, malates, methanesulfonates, benzenesulfonates, p-toluenesulfonates, etc. Preferred examples of salts with basic amino acids include salts with arginine, lysine, ornithine, etc. Preferred examples of salts with acidic amino acids include aspartates, glutamates, etc.

Among others, more preferred are pharmaceutically acceptable salts. For example, for the compound having an acidic functional group in the molecule, mentioned are their inorganic salts, such as alkali metal salts (e.g., sodium salts, potassium salts, etc.), and alkaline earth metal salts (e.g., calcium salts, magnesium salts, barium salts, etc.), ammonium salts, etc.; and for the compound having a basic functional group in the molecule, mentioned are their salts with inorganic acids such as hydrobromides, nitrates, sulfates, phosphates, etc., and with organic acids such as acetates, phthalates, oxalates, tartarates, maleates, citrate, succinates, methanesulfonates, p-toluenesulfonates, etc.

Processes for Producing Compound (I) are Mentioned Below.

Compound (I) can be produced by reacting a compound represented by the formula:

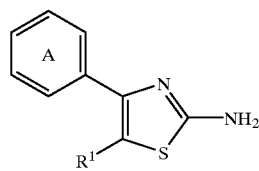

wherein each symbol is as defined above, or a salt thereof with a compound represented by the formula:

$R^2$—C≡C—COOH wherein $R^2$ is as defined above, or a salt thereof or a reactive derivative thereof, or a compound represented by the formula:

NCCHR³COOH wherein $R^3$ is as defined above, or a salt thereof or a reactive derivative thereof.

Examples of the reactive derivative to be used include a compound whose carboxyl group is esterified with $C_{1-6}$ alkyl (e.g., methyl, ethyl, propyl, isopropyl, etc.), $C_{6-10}$ aryl (e.g., phenyl, naphthyl, etc.), etc., an acid halide such as an acid chloride, an acid anhydride, and the like.

More specifically, compound (I) can be obtained by, for example, a process represented by the following Scheme 1 or its modification or, for example, modification of the process described in Journal of Heterocyclic Chemistry, Vol. 25, pp. 949–953 (1988); ibid., Vol. 28, pp. 489–492 (1991); JP 52-148096 A or GB 1345148; or the like.

In the following Scheme 1, R' and R" is hydrogen atom, $C_{1-6}$ alkyl (e.g., methyl, ethyl, propyl, isopropyl, etc.) or $C_{6-10}$ aryl (e.g., phenyl, naphthyl, etc.) and other symbols are as defined above. The compounds in the Scheme also include those in the form of salts and examples of the salts include the same salts as those exemplified with respect to compound (I) and the like.

Scheme 1

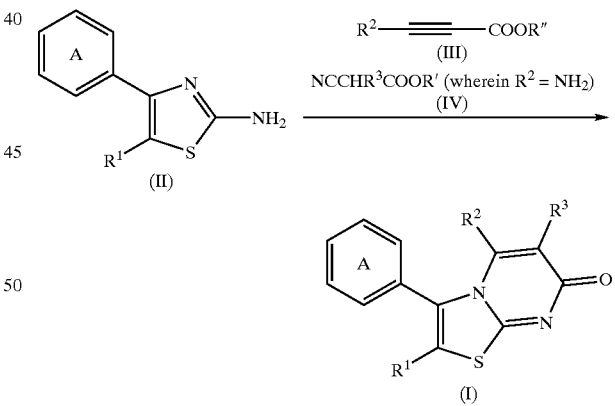

Compound (II) can be obtained by a per se known process, for example, that described in JP 60-58981 A, JP 61-10580 A, JP 7-503023 A, WO 93/15071, DE-A-3601411, JP 5-70446 A or the like, or its modification.

Compounds (III) and (IV) can be used commercial sources if they are commercially available or can be produced in any per se known process.

Compound (I) is obtained by subjecting compound (II) to condensation with an acetylenecarboxylic acid (III) or its reactive derivative, if desired, in the presence of an acid or a base.

The amount of compound (III) to be used is about 0.5 to about 3.0 mols, preferably about 0.8 to about 2.0 mols, relative to one mol of compound (II).

The amount of the acid or base to be used is about 1.0 to about 30 mols, preferably about 1.0 to about 10 mols, relative to one mol of compound (II).

The "acid" includes, for example, phosphoric acids such as polyphosphoric acid, etc.; sulfonic acids such as methanesulfonic acid, p-toluenesulfonic acid, etc.; organic acids such as acetic acid, etc.; mineral acids such as hydrochloric acid, hydrobromic acid, sulfuric acid, etc.; and the like.

The "base" includes, for example, basic salts such as sodium carbonate, potassium carbonate, cesium carbonate, etc.; inorganic bases such as sodium hydroxide, potassium hydroxide, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, is potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc.; and the like.

This reaction is advantageously carried out in the absence of a solvent or in an inert solvent. There is no particular limitation on the kind of solvent that can be used unless the reaction is interfered with. Examples of the solvent to be used include halogenated hydrocarbons, aliphatic hydrocarbons, aromatic hydrocarbons, ethers, amides, alcohols, polyphosphoric acids, organic acids, water, and mixtures of two or more of those solvents.

The reaction temperature is generally about −5 to about 200° C., preferably about 5 to about 150° C. The reaction time is generally about 5 minutes to about 72 hours, preferably about 0.5 to about 30 hours.

The product can be isolated from the reaction mixture in any ordinary manner. This can be easily purified through separation means such as recrystallization, distillation, chromatography and the like.

In addition, compound (I) is obtained by subjecting compound (II) to condensation with a cyanoacetic acid (IV) or its reactive derivative, if desired, in the presence of an acid or a base.

The amount of compound (IV) to be used is about 0.5 to about 3.0 mols, preferably about 0.8 to about 2.0 mols, relative to one mol of compound (II).

The amount of the acid or base to be used is about 1.0 to about 30 mols, preferably about 1.0 to about 10 mols, relative to one mol of compound (II).

The "acid" includes, for example, phosphoric acids such as polyphosphoric acid, etc.; organic acids such as acetic acid, etc.; and the like.

The "base" includes, for example, basic salts such as sodium carbonate, potassium carbonate, cesium carbonate, etc.; inorganic bases such as sodium hydroxide, potassium hydroxide, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc.; and the like.

This reaction is advantageously carried out in the absence of a solvent or in an inert solvent. There is no particular limitation on the kind of solvent that can be used unless the reaction is interfered with. Examples of the solvent to be used include halogenated hydrocarbons, aliphatic hydrocarbons, aromatic hydrocarbons, ethers, amides, alcohols, polyphosphoric acids, organic acids, water, and mixtures of two or more of those solvents.

The reaction temperature is generally about −5 to about 200° C., preferably about 5 to about 150° C. The reaction time is generally about 5 minutes to about 72 hours, preferably about 0.5 to about 30 hours.

The product can be isolated from the reaction mixture in any ordinary manner. This can be easily purified through separation means such as recrystallization, distillation, chromatography and the like.

Further, as shown by the following Scheme 2, compound (I) can be obtained from compound (V) and a metal cyanide compound (VI).

Scheme 2

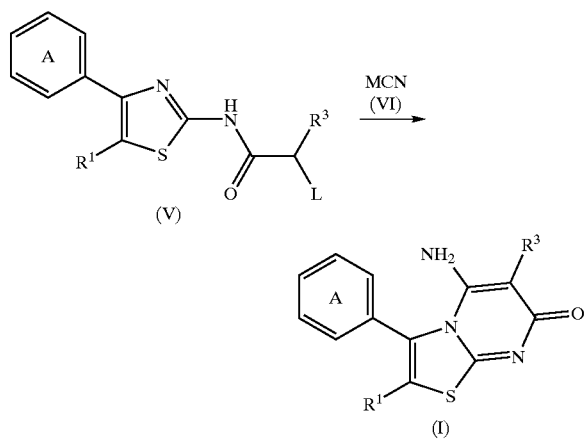

wherein L is a leaving group, M is a metal and other symbols are as defined above.

Examples of the leaving group as L include halogen atom (e.g., fluorine, chlorine, bromine, iodine, etc.), $C_{1-5}$ alkylsulfonyloxy which may be halogenated (e.g., methanesulfonyloxy, ethanesulfonyloxy, trichloromethanesulfonyloxy, etc.), $C_{6-14}$ arylsulfonyloxy (e.g., p-toluenesulfonyloxy, benzenesulfonyloxy, etc.), and the like.

Examples of the metal as M include sodium, potassium, copper, and the like.

The compounds in the Scheme also include those in the form of salts and examples of the salts include the same as those exemplified with respect to compound (I).

Compound (V) can be obtained by a per se known process, for example, that described in JP 60-58981 A, JP 61-10580 A, JP 7-503023 A, WO 93/15071, DE-A-3601411, JP 5-70446 A or the like, or its modification.

Compound (VI) can be used commercial sources if they are commercially available or can be produced in any per se known process.

The amount of compound (VI) to be used is about 0.5 to about 5.0 mols, preferably about 0.8 to about 3.0 mols, relative to one mol of compound (IV).

This reaction is advantageously carried out in the absence of a solvent or in an inert solvent. There is no particular limitation on the kind of solvent that can be used unless the reaction is interfered with. Examples of the solvent to be used include ethers, aromatic hydrocarbons, aliphatic hydrocarbons, amides, halogenated hydrocarbons, nitrites, sulfoxides, ketones, aromatic amines, alcohols, water, and mixtures of two or more of those solvents.

The reaction temperature is generally about −5 to about 200° C., preferably about 5 to about 50° C. The reaction time is generally about 5 minutes to about 72 hours, preferably about 0.5 to about 15 hours.

The product can be isolated from the reaction mixture in any ordinary manner. This can be easily purified through separation means such as recrystallization, distillation, chromatography and the like.

In the above-mentioned reactions where the starting compounds are substituted by any of amino, carboxy or hydroxy, those groups may be protected by ordinary protective groups which are generally used in peptide chemistry. The protective groups may be removed after the reaction to give the desired products.

The amino-protecting group includes, for example, formyl, $C_{1-6}$ alkyl-carbonyl (e.g., acetyl, propionyl, etc.) which may be substituted, phenylcarbonyl which may be substituted, $C_{1-6}$ alkoxy-carbonyl (e.g., methoxycarbonyl, ethoxycarbonyl, etc.) which may be substituted, phenyloxycarbonyl which may be substituted, $C_{7-10}$ aralkyloxycarbonyl (e.g., benzyloxycarbonyl, etc.) which may be substituted, trityl which may be substituted, phthaloyl which may be substituted, etc. These substituents include, for example, halogen atoms (e.g., fluorine, chlorine, bromine, iodine, etc.), $C_{1-6}$ alkyl-carbonyl (e.g., acetyl, propionyl, valeryl, etc.), nitro, etc. The number of those substituents is 1 to 3.

The carboxy-protecting group includes, for example, $C_{1-6}$ alkyl (e.g., methyl, ethyl, propyl, isopropyl, butyl, tert-butyl, etc.) which may be substituted, phenyl which may be substituted, trityl which may be substituted, silyl which may be substituted, etc. These substituents includes, for example, halogen atoms (e.g., fluorine, chlorine, bromine, iodine, etc.), formyl, $C_{1-6}$ alkyl-carbonyl (e.g., acetyl, propionyl, butylcarbonyl, etc.), nitro, $C_{1-6}$ alkyl (e.g., methyl, ethyl, tert-butyl, etc.), $C_{6-10}$ aryl (e.g., phenyl, naphthyl, etc.), etc. The number of those substituents is 1 to 3.

The hydroxy-protecting group includes, for example, $C_{1-6}$ alkyl (e.g., methyl, ethyl, propyl, isopropyl, butyl, tert-butyl, etc.) which may be substituted, phenyl which may be substituted, $C_{7-11}$ aralkyl (e.g., benzyl, etc.) which may be substituted, formyl which may be substituted, $C_{1-6}$ alkyl-carbonyl (e.g., acetyl, propionyl, etc.) which may be substituted, phenyloxycarbonyl which may be substituted, $C_{7-11}$ aralkyloxy-carbonyl (e.g., benzyloxycarbonyl, etc.) which may be substituted, tetrahydropyranyl which may be substituted, tetrahydrofuranyl which may be substituted, silyl which may be substituted, etc. Those substituents include, for example, halogen atoms (e.g., fluorine, chlorine, bromine, iodine, etc.), $C_{1-6}$ alkyl (e.g., methyl, ethyl, tert-butyl, etc.), $C_{7-11}$ aralkyl (e.g., benzyl, etc.), $C_{6-10}$ aryl (e.g., phenyl, naphthyl, etc.), nitro, etc. The number of those substituents is 1 to 4.

Those protective groups may be removed by any per se known methods or analogous methods thereto, such as treatment with acids, bases, ultraviolet rays, hydrazine, phenylhydrazine, sodium N-methyldithiocarbamate, tetrabutylammonium fluoride, palladium acetate, etc.; and reduction, etc.

In any case, if desired, products formed in the reaction mixtures may further be subjected to deprotection, acylation, alkylation, hydrogenation, oxidation, reduction, chain extension, substituents-exchange reaction and combined reactions thereof, to obtain compound (I). These methods include, for example, the methods described in "Shin Jikken Kagaku Kouza (New Edition of Lectures of Experimental Chemistry)" 14, 15 (1977) edited by Maruzen.

The above "alcohols" include, for example, methanol, ethanol, propanol, isopropanol, tert-butanol, etc.

The above "ethers" include, for example, diethyl ether, diisopropyl ether, diphenyl ether, tetrahydrofuran, dioxane, 1,2-dimethoxyethane, etc.

The above "halogenated hydrocarbons" include, for example, dichloromethane, chloroform, 1,2-dichloroethane, carbon tetrachloride, etc.

The above "aliphatic hydrocarbons" include, for example, hexane, pentane, cyclohexane, etc.

The above "aromatic hydrocarbons" include, for example, benzene, toluene, xylene, chlorobenzene, etc.

The above "aromatic amines" include, for example, pyridine, lutidine, quinoline, etc.

The above "amides" include, for example, N,N-dimethylformamide, N,N-dimethylacetamide, hexamethylphosphoric triamide, etc.

The above "ketones" include, for example, acetone, methyl ethyl ketone, etc.

The above "sulfoxides" include, for example, dimethylsulfoxide, etc.

The above "nitriles" include, for example, acetonitrile, propionitrile, etc.

The above "organic acids" include, for example, acetic acid, propionic acid, trifluoroacetic acid, etc.

Where the products are formed in their free form in the above reaction, they may be converted into their salts in any ordinary manner. Where they are formed in the form of their salts, they may be converted into free forms or other salts in any ordinary manner. The thus-obtained compound (I) may be isolated and purified from the reaction mixtures through any ordinary means of, for example, trans-salvation, concentration, solvent extraction, fractionation, crystallization, recrystallization, chromatography and the like.

Compound (Ia) other than compound (I) can be produced by the process for producing compound (I) or a per se known process or their modified processes.

Where compounds (I) and (Ia) exist in the form of their configurational isomers, diastereomers, conformers or the like, they may be optionally isolated into single isomers through the separation and isolation means mentioned above. Where compounds (I) and (Ia) are in the form of its racemates, they may be separated into S— and R— forms through any ordinary optical resolution.

Where compounds (I) and (Ia) exist in the form of stereoisomers or tautomers, both single isomers and mixtures of different isomers are included within the scope of the present invention. For example, when compound (I) have amino group at 5-position of the thiazolopyrimidine ring, a compound represented by the formula:

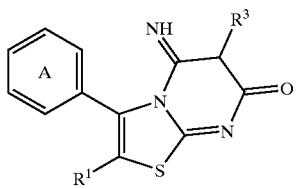

(I')

wherein each symbol is as defined above, is included in the scope of compound (I) of the present invention.

Similarly, when compound (Ia) have amino group at 5-position of the thiazolopyrimidine ring, a compound represented by the formula:

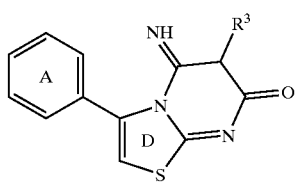

(Ia')

where each symbol is as defined above, is included in the scope of compound (Ia) of the present invention.

Specifically, the followings are used as compound (I') or compound (Ia'):

1) 5-imino-3-(4-metoxyphenyl)-2-(4-pyridyl)-5,6-dihydro-7H-thiazolo[3,2-a]pyrimidin-7-one, 2) 5-imino-3-[4-(1,1-dimethylethyl)phenyl]-2-(4-pyridyl)-5,6-dihydro-7H-thiazolo[3,2-a]pyrimidin-7-one, 3) 5-imino-3-(3,5-dimethylphenyl)-2-(4-pyridyl)-5,6-dihydro-7H-thiazolo[3,2-a]pyrimidin-7-one, and the like.

Further, compounds (I) and (Ia) may be in any form of their hydrates and non-hydrates.

Prodrugs of compounds (I) and (Ia) mean compounds that are converted into compounds (I) and (Ia) by a reaction with an enzyme, gastric acid, or the like under a physiological condition in a living body, namely, compounds that are converted into compounds (I) and (Ia) by an enzymatic oxidation, reduction, hydrolysis, or the like or compounds that are converted into compound (I) and (Ia) by hydrolysis with gastric acid or the like. Examples of the prodrug of compound (I) or (Ia) include a compound where the amino group in a compound (I) or (Ia) is acylated, alkylated, or phosphorylated (e.g., a compound where the amino group in compound (I) or (Ia) is converted into eicosanoylamino, alanylamino, pentylaminocarbonylamino, (5-methyl-2-oxo-1,3-dioxolan-4-yl)methoxycarbonylamino, tetrahydrofuranylamino, pyrrolidylmethylamino, pivaloyloxymethylamino, or tert-butylamino, etc.); a compound where the hydroxyl group in compound (I) or (Ia) is acylated, alkylated, phosphorylated, or converted into the borate (e.g., a compound where the hydroxyl group in compound (I) or (Ia) is converted into acetyloxy, palmitoyloxy, propanoyloxy, pivaloyloxy, succinyloxy, fumaryloxy, alanyloxy, or dimethylaminomethylcarbonyloxy, etc.); a compound where the carboxyl group in compound (I) or (Ia) is esterified or amidated (e.g., a compound where the carboxyl group in compound (I) or (Ia) is subjected to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolan-4-yl) methyl esterification, cyclohexyloxycarbonylethyl esterification, or conversion into the methyl amide, etc.), and the like. These compounds can be produced from compounds (I) and (Ia) according to a well-known method.

Also, the prodrug of compounds (I) or (Ia) may be a compound that is converted into compound (I) or (Ia) under a physiological condition as described in "Iyakuhin No Kaihatu (Development of Drugs)", Volume 7, Molecular Design, Hirokawa Shoten, published in 1990; page 163 to page 198.

The agent of the present invention comprising compound (I) or (Ia) shows a high affinity for adenosine receptor, especially for adenosine $A_3$ receptor, while having low toxicity and few side effects. The agent is useful as a safe medicine.

The agent of the present invention comprising compound (I) or (Ia) has a potent adenosine $A_3$ receptor antagonistic activity on mammals (e.g., mouse, rat, hamster, rabbit, cat, dog, bovine, sheep, monkey, human, etc.), a good oral absorption, a good metabolical stability, and therefore, it can be used for preventing and/or treating diseases that may be related to adenosine $A_3$ receptor, for example, asthma, allergic disease, inflammation, Addison's disease, autoimmune hemolytic anemia, Crohn's disease, psoriasis, rheumatism, central nerve diseases (e.g., cerebrovacular disorders such as haemorrhagia cerebri, cerebral infarction, etc., head injury, spinal injury, cerebral edema, etc.), diabetes, and so on. Preferred is an agent for prevention and/or treatment of central nerve diseases, asthma, allergic disease, etc.

The agent of the present invention comprising compound (I) or (Ia) has low toxicity, and therefore, compound (I) or (Ia) is, either directly as it is or after having been formulated into pharmaceutical compositions along with pharmaceutically acceptable carriers in any per se known manner, for example, into tablets (including sugar-coated tablets, film-coated tablets), powders, granules, capsules (including soft capsules), liquid preparations, injections, suppositories, sustained release preparations, etc., safely administered orally or parenterally (e.g., locally, rectally, intravenously, etc.). In the pharmaceutical composition of the present invention, the amount of compound (I) or (Ia) is from about 0.01 to about 100% by weight based on the total weight of the composition. The dose of the composition varies, depending on the subject to which the composition is administered, the administration route employed, the disorder of the subject, etc. For example, as an adenosine $A_3$ receptor antagonist, oral composition for treating asthma, its dose for adults (body weight ca. 60 kg) may be from about 0.1 to about 30 mg/kg of body weight, preferably from about 1 to about 20 mg/kg of body weight, in terms of the active ingredient (compound (I) or (Ia)), and this may be administered once or divided into several times a day.

Any ordinary organic and inorganic carrier substances that are generally used in formulating medicines are usable as the carriers for formulating the pharmaceutical compositions of the present invention. For example, employable are ordinary excipients, lubricants, binders, disintegrators, etc. for formulating solid preparations; and solvents, solubilizers, suspending agents, isotonizing agents, buffers, soothing agents, etc. for formulating liquid preparations. If desired, further employable are other additives such as preservatives, antioxidants, colorants, sweeteners, adsorbents, wetting agents, etc.

The excipients include, for example, lactose, white sugar, D-mannitol, starch, corn starch, crystalline cellulose, light silicic anhydride, etc.

The lubricants include, for example, magnesium stearate, calcium stearate, talc, colloidal silica, etc.

The binders include, for example, crystalline cellulose, white sugar, D-mannitol, dextrin, hydroxypropyl cellulose, hydroxypropylmethyl cellulose, polyvinyl pyrrolidone, starch, sucrose, gelatin, methyl cellulose, carboxymethyl cellulose sodium, etc.

The disintegrators include, for example, starch, carboxymethyl cellulose, carboxymethyl cellulose calcium, croscarmellose sodium, carboxymethyl starch sodium, L-hydroxypropyl cellulose, etc.

The solvents include, for example, water for injections, alcohol, propylene glycol, macrogol, sesame oil, corn oil, olive oil, etc.

The solubilizers include, for example, polyethylene glycol, propylene glycol, D-mannitol, benzyl benzoate, ethanol, trisaminomethane, cholesterol, triethanolamine, sodium carbonate, sodium citrate, etc.

The suspending agents include, for example, surfactants such as stearyl triethanolamine, sodium lauryl sulfate, lauryl aminopropionic acid, lecithin, benzalkonium chloride, benzethonium chloride, glycerin monostearate, etc.; hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose, etc.

The isotonizing agents include, for example, glucose, D-sorbitol, sodium chloride, glycerin, D-mannitol, etc.

The buffers include, for example, liquid buffers of phosphates, acetates, carbonates, citrates, etc.

The soothing agents include, for example, benzyl alcohol, etc.

The preservatives include, for example, parahydroxybenzoates, chlorobutanol, benzyl alcohol, phenethyl alcohol, dehydroacetic acid, sorbic acid, etc.

The antioxidants include, for example, sulfites, ascorbic acid, α-tocopherol, etc.

The present invention will be described in more detail hereinunder, with reference to the following Reference Examples, Examples, Formulation Examples and Experimental Examples, which, however, are to concretely illustrate some embodiments of the invention and are not intended to restrict the scope of the invention. Various changes and modifications can be made within the range that does not deviate the scope of the invention.

"Room temperature" as referred to in the following Reference Examples and Examples is meant to indicate a temperature falling between about 10° C. and about 35° C. Unless otherwise specifically indicated, "%" is by weight. The yield indicates mol/mol %.

The meanings of the abbreviations used hereinunder are as follows:

s: singlet
d: doublet
br: broad
J: coupling constant
Hz: Hertz
$CDCl_3$: deuterated chloroform
$^1H$—NMR: proton nuclear magnetic resonance spectrum
DMSO: dimethylsulfoxide-$d_6$

REFERENCE EXAMPLE 1

[4-(4-Methoxyphenyl)-5-(4-pyridyl)-1,3-thiazol-2-yl]amine

2-Bromo-2-phenyl-1-(4-pyridyl)ethanone hydrobromide (11.0 g) was suspended in a suspension of thiourea (2.22 g) in acetonitrile (170 mL), and triethylamine (4.1 mL) was slowly added dropwise thereto with stirring. After completion of the addition, the mixture was stirred at refluxing temperature for 3 hours and then the solvent was distilled off. Aqueous saturated sodium hydrogen carbonate solution was added to the residue and the deposit was filtered off. The remaining mixture was washed with water and ethyl ether and dried. The crude crystals obtained were recrystallized from pyridine to obtain the title compound (5.48 g, yield 68%).

m.p. 282–284° C.

REFERENCE EXAMPLE 2

(1) Reference Example Compound 2-1
[4-[4-(1,1-Dimethylethyl)phenyl]-5-(4-pyridyl)-1,3-thiazol-2-yl]amine
m.p. 254–257° C. (ethanol).

(2) Reference Example Compound 2-2
[4-(3,5-Dimethylphenyl)-5-(4-pyridyl)-1,3-thiazol-2-yl]amine
m.p. 242–244° C. (ethanol).

According to the same manner as that described in Reference Example 1, the above Reference Example Compounds 2-1 and 2-2 were synthesized except that 2-bromo-2-[4-(1,1-dimethylethyl)phenyl]-1-(4-pyridyl)ethanone hydrobromide and 2-bromo-2-(3,5-diemthylphenyl)-1-(4-pyridyl)ethanone hydrobromide were used, respectively, instead of 2-bromo-2-(4-methoxyphenyl)-1-(4-pyridyl) ethanone hydrobromide.

REFERENCE EXAMPLE 3

N-[4-[4-(1,1-Dimethylethyl)phenyl]-5-(4-pyridyl)-1,3-thiazol-2-yl]-2-chloroacetamide Hydrochloride Chloroacetyl chloride (0.55 g, 4.85 mmol) was added to a solution of [4-[4-(1,1-dimethylethyl)phenyl]-5-(4-pyridyl)-1,3-thiazol-2-yl]amine (1.0 g, 3.23 mmol) in N,N-dimethylacetaminde (10 mL) and the mixture was stirred at 60° C. for 14 hours. The solvent was concentrated under reduced pressure and the resultant residue was washed with ether and dried. The crude crystals obtained was recrystalized from ethanol to obtain the title compound (0.94 g, yield 69%).

m.p. 267–269° C.

EXAMPLE 1

5-Amino-3-(4-methoxyphenyl)-2-(4-pyridyl)-7H-thiazolo[3,2-a]pyrimidin-7-one

To a suspension of [4-(4-methoxyphenyl)-5-(4-pyridyl)-1,3-thiazol-2-yl]amine (1.0 g) in ethanol were added in turn a 20% solution of sodium ethoxide in ethanol (1.4 mL) and ethyl cyanoacetate (0.40 g). The resultant mixture was heated under reflux for 8 hours. After distilling off the solvent, water was added to the residue, the mixture was neutralized with acetic acid and the precipitate formed was filtered off. The remaining crude crystals were recrystallized from ethanol to obtain the title compound (0.52 g, yield 42%).

mp 267–271° C. $^1$H-NMR (DMSO-$d_6$) δ: 3.78 (3H, s), 4.10 (2H, br s), 6.94 (2H, d, J=8.8 Hz), 7.29 (2H, d, J=6.1 Hz), 7.37 (2H, d, J=8.8 Hz), 8.53 (2H, d, J=6.1 Hz), 12.81 (1H, br s).

EXAMPLE 2

5-Amino-3-[4-(1,1-dimethylethyl)phenyl]-2-(4-pyridyl)-7H-thiazolo[3,2-a]pyrimidin-7-one To a solution of N-[4-[4-(1,1-dimethylethyl)phenyl]-5-(4-pyridyl)-1,3-thiazol-2-yl]-2-chloroacetamide hydrochloride (1.0 g) in dimethylsulfoxide (5 mL) was added sodium cyanate (0.24 g). The mixture was stirred at room temperature for 14 hours. An aqueous solution of sodium hydrogen carbonate was added to the reaction mixture and the mixture was extracted with a mixed solvent of ethyl acetate-tetrahydrofuran (1:1). The extract was washed with brine, dried over anhydrous sodium sulfate and filtered. The solvent was concentrated under reduced pressure and the residue was purified with silica gel column chromatography (hexane-tetrahydrofuran, 1:1) and recrystallized from ethyl acetate to obtain the title compound (0.14 g, yield 24%).

mp 259–262° C. $^1$H-NMR (CDCl$_3$) δ: 1.36 (9H, s), 2.66 (2H, s), 7.25 (2H, d, J=5.9 Hz), 7.44 (2H, s), 8.57 (2H, d, J=5.9 Hz).

EXAMPLE 3

5-Amino-3-(3,5-dimethylphenyl)-2-(4-pyridyl)-7H-thiazolo[3,2-a]pyrimidin-7-one

To a solution of [4-(3,5-dimethylphenyl)-5-(4-pyridyl)-1,3-thiazol-2-yl)amine (1.0 g) in N,N-dimethylacetamide (10 mL) was added chloroacetyl chloride (0.60 g) and the mixture was stirred at 80° C. for 14 hours. N,N-Dimethylacetamide was distilled off under reduced pressure and the resultant residue was dissolved in dimethylsulfoxide (5 mL). To this solution was added sodium cyanate (0.24 g) and the mixture was stirred at room temperature for 14 hours. An aqueous solution of sodium hydrogen carbonate was added to the reaction mixture and the mixture was extracted with a mixed solvent of ethyl acetate-tetrahydrofuran (1:1). The extract was washed with brine, dried over anhydrous sodium sulfate and filtered. The solvent was concentrated under reduced pressure and the residue was purified by silica gel column chromatography (hexane-tetrahydrofuran, 1:1) and recrystallized from ethanol to obtain the title compound (0.22 g, yield 18%).

mp 275–278° C. $^1$H—NMR (CDCl$_3$) δ: 2.26 (6H, s), 3.73 (2H, s), 6.99 (1H, s), 7.06 (2H, s), 7.23 (2H, d, J=6.2 Hz), 8.50 (2H, d, J=6.2 Hz).

The chemical structural formulas of the compounds obtained in Examples 1 to 3 are shown below.

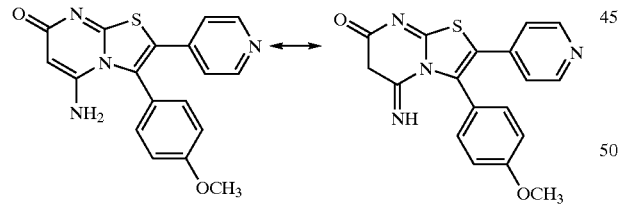

EXAMPLE 1 COMPOUND

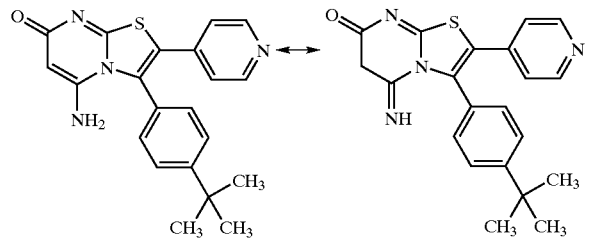

EXAMPLE 2 COMPOUND

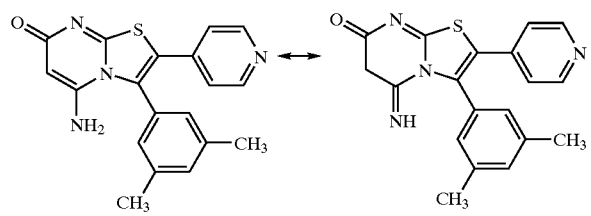

EXAMPLE 3 COMPOUND

FORMULATION EXAMPLE 1

| | |
|---|---|
| (1) Example 1 | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Calcium carboxymethyl cellulose | 20 mg |
| Total | 120 mg |

(1) to (6) were mixed in an ordinary manner, and tabletted into tablets using a tabletting machine.

EXPERIMENTAL EXAMPLE 1

The following procedures in this Example were carried out according to the methods described in Molecular Cloning —Cold Spring Harbor Laboratory (1989) or protocol specified by manufacturers.
(1) Cloning of Human Adenosine A$_3$ Receptor Cloning of the human adenosine A$_3$ receptor gene was carried out by the polymerase chain reaction (PCR) from human brain cDNA. Using 1 ng of brain cDNA (Quick-Clone cDNA, TOYOBO, Osaka) as template, PCR was performed in DNA Thermal Cycler 480 (Perkin Elmer) (reaction conditions: 35 cycles of 1 min at 95° C., 1 min at 66° C., and 2 min at 75° C.) by mixing primers (50 pmol each), 5'-CGCCTCTAGACAAGATGCCCAACAACAGCA TGC-3' [Sequence No. 1] and 5'-CGGGGTCGACACTACTCAGAATTCTTCT CAATGC-3' [Sequence No. 2], which were designed referring to nucleotide sequence of adenosine A$_3$ receptor gene reported by Salvatore et. al., (Proc. Natl. Acad. Sci. U. S. A., 90:10365–10369, 1993) and TaKaRa LA PCR Kit Ver.2 (TaKaRa Shuzo Co. Ltd., Kyoto). The PCR product was electrophoresed and 1.0 kb DNA fragment was recovered. The DNA fragment encoding adenosine A$_3$ receptor was cloned using Original TA Cloning Kit (FUNAKOSHI, Tokyo).

Thus obtained plasmid was digested with Xba I (TaKaRa Shuzo Co. Ltd., Kyoto), blunted with T4 DNA polymerase (TaKaRa Shuzo Co. Ltd., Kyoto) and digested with Sal I (TaKaRa Shuzo Co. Ltd., Kyoto) to obtain adenosine A$_3$ receptor gene fragment.
(2) Construction of Human Adenosine A$_3$ Receptor Expression Plasmid The SRα promoter from pTB1411 disclosed in JP 5-076385 A was ligated into the pCI vector (Promega, Tokyo), which was digested with Bgl II (TaKaRa Shuzo Co. Ltd., Kyoto), blunted and digested with EcoRI (TaKaRa Shuzo Co. Ltd., Kyoto) subsequently. The resulting plasmid, designated as pCI-SRα, was then digested with Cla I (TaKaRa Shuzo Co. Ltd., Kyoto) and blunted with T4 DNA polymerase (TaKaRa Shuzo Co. Ltd., Kyoto). On the other hand, pGFP-C1 (TOYOBO, Osaka) was digested with Bsu 36I (DAIICHIKAGAKUYAKUHIN, Tokyo) and the 1.63 kb fragment was recovered after the blunting with T4 DNA polymerase. Both were ligated to the pCI-SRα vector using DNA Ligation kit (TaKaRa Shuzo Co. Ltd., Kyoto). The ligation mixture was used to transform *E. coli* JM109 competent cells (TaKaRa Shuzo Co. Ltd., Kyoto). The resulting plasmid thus obtained was designated as pMSRαneo.

pMSRαneo was digested with EcoRI (TaKaRa Shuzo Co. Ltd., Kyoto), blunted with T4 DNA polymerase (TaKaRa Shuzo Co. Ltd., Kyoto) and then digested with Sal I (TaKaRa Shuzo Co. Ltd., Kyoto) to obtain DNA at size of 5.4 kb. This was ligated with adenosine $A_3$ receptor obtained in the above (1) by using DNA Ligation kit (TaKaRa Shuzo Co. Ltd., Kyoto). The ligation mixture was used to transform *E. coli* JM109 competent cells (TaKaRa Shuzo Co. Ltd., Kyoto). The plasmid thus obtained was designated as pA3SRα.

(3) Transfection of Adenosine $A_3$ Receptor Expression Plasmid into CHO (dhfr⁻) and the Expression CHO (dhfr⁻) cells were grown on Ham's F-12 medium (Nihon Seiyaku, Tokyo) supplement with 10% fetal bovine serum (Life Tech Oriental; Life Technologies, Inc., Rockville, Md., USA) in a 750 ml Tissue culture flask (Becton Dickinson, Mt. View, Calif.). The growing cells were treated with 0.5 g/L trypsin-0.2 g/L EDTA (Life Technologies, Inc., Rockville, Md., USA) to harvest, washed with PBS (phosphate buffered physiological saline, Life Technologies, Inc., Rockville, Md., USA), centrifugated at 1000 rpm for 5 min, and suspended in PBS.

Transfection with DNA into the cells was performed by using a Gene Pulser (Bio-Rad) under the following conditions. Namely, $8 \times 10^6$ cells and the plasmid pA₃SRα for expression of human adenosin $A_3$ receptor were added to a 0.4 cm gap cuvette and electroporation was performed in a volume of 0.8 mL at voltage of 0.25 kV, and capacitance of 960 μF. The transfected cells were transferred into Ham's F-12 medium containing 10% fetal bovine serum, cultivated for 24 hours, harvested, suspended in Ham's F-12 media supplement with 10% fetal bovine serum and 500 μg/ml geneticin (Life Technologies Inc., Rockville, Md., USA) at a cell density of $10^4$ cells/mL. The cells were plated onto 96 well plates (Becton Dickinson) containing Ham's F-12 media supplement with 10% fetal bovine serum and 500 μg/mL geneticin (Life Technologies Inc., Rockville, Md., USA) at a cell density of $10^4$ cells/mL.

The geneticin resistant cells thus obtained were further cultivated on 24 well plates (Becton Dickinson) and the cells expressing adenosine $A_3$ receptor were selected from them as follows. The cells were incubated in assay buffer I (HBSS (Hanks' balanced salt solution, Wako chemicals, Osaka) containing 0.1% BSA (bovine serum albumin), 0.25 mM PMSF (phenylmethylsulfonyl fluoride), 1 μg/mL pepstatin, and 20 ug/mL leupeptin) to which was added 50 pM ¹²⁵I-AB-MECA (4-aminobenzyl-5'-N-methylcarboxamide adenosine, Amersham) as ligand, for 1 hour, and washed with assay buffer I. The radioactivity associated with the cell was measured in a y-counter to select A₃AR/CHO cells which specifically bind to the ligand.

(4) Cell Membrane Preparation of the Transfectant Expressing Adenosine $A_3$ Receptor After A₃AR/CHO cells obtained in the above (3) were cultivated in Ham's F-12 medium containing 10% fetal bovine serum for 2 days, the cells were treated with PBS plus 0.02% EDTA, centrifuged to collect, resuspended in assay buffer II (50 mM Tris-HCl (pH7.5), 1 mM EDTA, 10 mM $MgCl_2$, 0.25 mM PMSF, 1 μg/mL pepstatin, and 20 μg/mL leupeptin) and homogenized using Polytron homogenizer (PT-3000, KINEMATICA AG: 20,000 rpm, 20 sec, 3 times). This suspension was centrifuged at 2,000 rpm for 10 min and supernatant fraction containing cell membranes was obtained. The supernatant fraction was ultra-centrifuged at 30,000 rpm (model L8-70M, rotor 70Ti, Beckman) for 1 hour.

Thus obtained pellet was resuspended in assay buffer II containing 2 unit/mL adenosine deaminase (Boehriger Mannheim) and incubated at 30° C. for 30 min. The suspension was ultra-centrifuged under the same condition as above and the cell membrane fraction was obtained as the pellet.

(5) Binding Assays with Adenosine $A_3$ Receptor 10 rM of [³H]-NECA (Amersham Life Sciences, Inc., Tokyo) as ligand was added to the reaction mixture including test compound at various concentration and 100 μg/mL of membranes obtained in (4) in assay buffer II. The reaction mixture was incubated for 1 hour at room temperature and filtrated through the Unifilter GF/C (Packard Instrument Company) to transfer the membrane onto the filter, using Cell Harvester (Packard Instrument Company). The filter was washed three times with ice-cold 50 mM Tris-HCl (pH 7.5), and dried. Then, Microscint-0 was placed on the filter and radioactivity retained on the filter was determined by Top-Count (Packard Instrument Company). The concentration that inhibits 50% specific binding ($IC_{50}$) to the membrane of [³H]-NECA were calculated by PRISM 2.01 (Graph Pad Software).

As a result, $IC_{50}$ value of Example Compound 1 was 3.5 nM. This result shows that the compound (I) has a high affinity for adenosine $A_3$ receptor.

INDUSTRIAL APPLICABILITY

Since compounds (I) and (Ia) have a excellent $A_3$ adenosine receptor antagonistic activity and are useful for preventing and/or treating adenosine $A_3$ receptor relating diseases.

What is claimed is:
1. A compound represented by the formula:

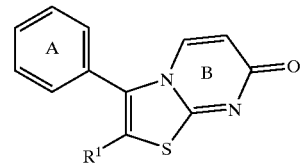

wherein:
ring A is a benzene ring which may have 1 to 5 substituents selected from the group consisting of (i) halogen atom, (ii) $C_{1-3}$ alkylenedioxy, (iii) nitro, (iv) cyano, (v) optionally halogenated $C_{1-6}$ alkyl, (vi) optionally halogenated $C_{2-6}$ alkenyl, (vii) carboxy $C_{1-6}$ alkyl, (viii) carboxy $C_{2-6}$ alkenyl, (ix) optionally halogenated $C_{2-6}$ alkynyl, (x) optionally halogenated $C_{3-6}$ cycloalkyl, (xi) $C_{6-14}$ aryl, (xii) optionally halogenated $C_{1-6}$ alkoxy, (xiii) $C_{1-6}$ alkoxy-carbonyl-$C_{1-6}$ alkoxy, (xiv) hydroxy, (xv) $C_{6-14}$ aryloxy, (xvi) $C_{7-16}$ aralkyloxy, (xvii) mercapto, (xviii) optionally halogenated $C_{1-6}$ alkylthio, (xix) $C_{6-14}$ arylthio, (xx) $C_{7-16}$ aralkylthio, (xxi) amino, (xxii) mono-$C_{1-6}$ alkylamino, (xxiii) mono-$C_{6-14}$ arylamino, (xxiv) mono-$C_{7-16}$ aralkylamino, (xxv)

di-C$_{7-16}$ aralkylamino, (xxvi) di-C$_{1-6}$ alkylamino, (xxvii) di-C$_{6-14}$ arylamino, (xxviii) formyl, (xxix) carboxy, (xxx) C$_{1-6}$ alkyl-carbonyl, (xxxi) C$_{3-6}$ cycloalkyl-carbonyl, (xxxii) C$_{1-6}$ alkoxy-carbonyl, (xxxiii) C$_{6-14}$ aryl-carbonyl, (xxxiv) C$_{7-16}$ aralkyl-carbonyl, (xxxv) C$_{6-14}$ aryloxy-carbonyl, (xxxvi) C$_{7-16}$ aralkyloxy-carbonyl, (xxxvii) 5- or 6-membered heterocyclic-carbonyl selected from the group consisting of nicotinoyl, isonicotinoyl, thienoyl, furoyl, morpholinocarbonyl, thiomorpholinocarbonyl, piperazin-1-ylcarbonyl and pyrrolidin-1-ylcarbonyl, (xxxviii) carbamoyl, (xxxix) thiocarbamoyl, (xxxx) mono-C$_{1-6}$ alkyl-carbamoyl, (xxxxi) di-C$_{1-6}$ alkyl-carbamoyl, (xxxxii) C$_{6-14}$ aryl-carbamoyl, (xxxxiii) 5- or 6-membered heterocylic carbamoyl selected from the group consisting of 2-pyridylcarbamoyl, 3-pyridylcarbamoyl, 4-pyridylcarbamoyl, 2-thienylcarbamoyl and 3-thienylcarbamoyl, (xxxxiv) C$_{1-6}$ alkylsulfonyl, (xxxxv) C$_{6-14}$ arylsulfonyl, (xxxxvi) formylamino, (xxxxvii) C$_{1-6}$ alkyl-carbonylamino, (xxxxviii) C$_{6-14}$ aryl-carbonylamino, (xxxxix) C$_{1-6}$ alkoxy-carbonylamino, (xxxxx) C$_{1-6}$ alkylsulfonylamino, (xxxxxi) C$_{6-14}$ arylsulfonylamino, (xxxxxii) C$_{1-6}$ alkyl-carbonyloxy, (xxxxxiii) C$_{6-14}$ aryl-carbonyloxy, (xxxxxiv) C$_{1-6}$ alkoxy-carbonyloxy, (xxxxxv) mono-C$_{1-6}$ alkyl-carbamoyloxy, (xxxxxvi) di-C$_{1-6}$ alkyl-carbamoyloxy, (xxxxxvii) C$_{6-14}$ aryl-carbamoyloxy, (xxxxxviii) nicotinoyloxy, (xxxxxix) 5- to 7-membered saturated cyclic amino which may be substituted by a substituent selected from the group consisting of C$_{1-6}$ alkyl, C$_{6-14}$ aryl, C$_{1-6}$ alkyl-carbonyl, oxo, and 5- to 10-membered aromatic heterocylic group selected from 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, or 3-benzo[b]furanyl, (xxxxxx) 5- to 10-membered aromatic heterocylic group selected from 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, or 3-benzo[b]furanyl, and (xxxxxxi) sulfo;

ring B may have 1 or 2 substituents selected from the same substituents as defined for ring A; and $R^1$ is C$_{3-6}$ cycloalkyl group, C$_{6-14}$ aryl group or a monovalent group formed by removing any one hydrogen atom from a 5- to 14-membered heterocyclic ring selected from the group consisting of (i) 5- to 14-membered aromatic heterocyclic ring selected from the group consisting of thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan and phenoxazine, and a ring formed by fusion of the 5- to 14-membered aromatic heterocyclic ring with one or two benzene rings, (ii) 5- to 10-membered aliphatic heterocyclic ring selected from the group consisting of pyrrolidine, imidazoline, pyrazolidine, pyrazoline, piperidine, piperazine, morpholine, thiomorpholine, dioxazole, oxadiazoline, thiadiazoline, triazoline, thiadiazole and dithiazole, and (iii) 7- to 10-membered bridged heterocyclic ring selected from the group consisting of quinuclidine and 7-azabicyclo[2.2.1]heptane; each of which may have 1 to 5-substitutents selected from the same substituents as defined for ring A;

or a salt thereof.

2. The compound according to claim 1, wherein $R^1$ is the monovalent group formed by removing any one hydrogen atom from the 5- to 14-membered heterocyclic ring.

3. The compound according to claim 1, wherein the monovalent group formed by removing any one hydrogen atom from the 5- to 14-membered heterocyclic ring is a 5- to 14-membered nitrogen-containing aromatic heterocyclic group.

4. The compound according to claim 1, wherein the monovalent group formed by removing any one hydrogen atom from the 5- to 14-membered heterocyclic ring is a 2-pyridyl group, 3-pyridyl group, 4-pyridyl group, 2-quinolyl group, 3-quinolyl group, 4-quinolyl group, 5-quinolyl group, 8-quinolyl group, 1-isoquinolyl group, 3-isoquinolyl group, 4-isoquinolyl group, 5-isoquinolyl group, pyrazinyl group, 2-pyrimidinyl group, 4-pyrimidinyl group, 3-pyrrolyl group, 2-imidazolyl group, 3-pyridazinyl group, 3-isothiazolyl group, 3-isoxazolyl group, 1-indolyl group, 2-indolyl group, 3-indolyl group or 2-benzothiazolyl group.

5. The compound according to claim 1, wherein the monovalent group formed by removing any one hydrogen atom from the 5- to 14-membered heterocyclic ring is a 5- or 6-membered nitrogen-containing aromatic heterocyclic group.

6. The compound according to claim 1, wherein the monovalent group formed by removing any one hydrogen atom from the 5- to 14-membered heterocyclic ring is a 2-pyridyl group, 3-pyridyl group, 4-pyridyl group, pyrazinyl group, 2-pyrimidinyl group, 4-pyrimidinyl group, 3-pyrrolyl group, 3-pyridazinyl group, 3-isothiazolyl group or 3-isoxazolyl group.

7. The compound according to claim 1, wherein the monovalent group formed by removing any one hydrogen atom from the 5- to 14-membered heterocyclic ring is a pyridyl group.

8. The compound according to claim 1, wherein $R^1$ is a 4-pyridyl group.

9. The compound according to claim 1, wherein $R^1$ is an optionally substituted nitrogen-containing aromatic heterocyclic group.

10. The compound according to claim 1, wherein ring A is a benzene ring which may be substituted with C$_{1-6}$ alkoxy, or one or two C$_{1-6}$ alkyls.

11. The compound according to claim 1, wherein ring A is a benzene ring which may be substituted with C$_{1-6}$ alkoxy.

12. The compound according to claim 1, wherein the substituent of ring B is amino.

13. The compound according to claim 1, wherein ring A is a benzene ring which may be substituted with C$_{1-6}$ alkoxy, or one or two C$_{1-6}$ alkyls, ring B may be substituted with amino, and $R^1$ is a pyridyl group.

14. The compound according to claim 1, wherein ring A is a benzene ring which may be substituted with C$_{1-6}$ alkoxy, ring B may be substituted with amino, and $R^1$ is a pyridyl group.

15. The compound according to claim 1 which is represented by the formula:

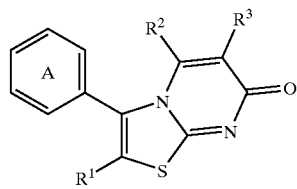

wherein $R^2$ and $R^3$ are the same or different, and are hydrogen atom or a substituent selected from the same substitutents as defined for ring A in claim 1, and ring A and $R^1$ are as defined in claim 1, or a salt thereof.

16. The compound according to claim 15, wherein $R^3$ is hydrogen atom.

17. (1) 5-amino-3-(4-methoxyphenyl)-2-(4-pyridyl)-7H-thiazolo[3,2-a]pyrimidin-7-one or its salt, (2) 5-amino-3-[4-(1,1-dimethylethyl)phenyl]-2-(4-pyridyl)-7H-thiazolo[3,2-a]pyrimidin-7-one or its salt, or (3) 5-amino-3-(3,5-dimethylphenyl)-2-(4-pyridyl)-7H-thiazolo(3,2-a]pyrimidin-7-one or its salt.

18. A prodrug of the compound according to claim 1, which is a hydrolyzable derivative of the compound according to claim 1.

19. A process for producing the compound according to claim 1 or a salt thereof, which comprises reacting a compound represented by the formula:

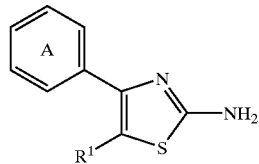

wherein ring A and $R^1$ are as defined in claim 1, or its salt, with a compound represented by the formula:

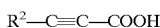

wherein $R^2$ is hydrogen or a substituent of ring B as defined in claim 1, or its salt or reactive derivative, or a compound represented by the formula:

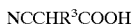

wherein $R^3$ is hydrogen or a substituent of ring B as defined in claim 1, or its salt or reactive derivative.

20. A pharmaceutical composition comprising a compound according to claim 1, or a salt thereof, together with a pharmaceutically acceptable carrier.

21. A pharmaceutical composition, which comprises a prodrug according to claim 18, or a salt thereof, together with a pharmaceutically acceptable carrier.

22. The prodrug according to claim 18, wherein the hydrolyzable derivative is an acylate, alkylate, amide, ester, phosphorylate or borate of the compound according to claim 1.

23. A method for treating asthma, which comprises administering to a mammal an effective amount of the compound according to claim 1, or a salt thereof, or a prodrug thereof which comprises a hydrolyzable derivative thereof.

* * * * *